US006764853B2

(12) United States Patent
Filpula et al.

(10) Patent No.: US 6,764,853 B2
(45) Date of Patent: Jul. 20, 2004

(54) METHOD FOR TARGETED DELIVERY OF NUCLEIC ACIDS

(75) Inventors: David R. Filpula, Piscataway, NJ (US); Maoliang Wang, East Brunswick, NJ (US); Marc D. Whitlow, El Sobrante, CA (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 189 days.

(21) Appl. No.: 09/983,580

(22) Filed: Oct. 25, 2001

(65) Prior Publication Data

US 2002/0151061 A1 Oct. 17, 2002

Related U.S. Application Data

(62) Division of application No. 09/420,592, filed on Oct. 19, 1999, now Pat. No. 6,333,396
(60) Provisional application No. 60/104,949, filed on Oct. 20, 1998.

(51) Int. Cl.$^7$ .................. C12N 15/09; C12N 15/00; C07K 16/00; A61K 48/00; C07H 21/04
(52) U.S. Cl. .................. 435/455; 435/468; 435/325; 435/320.1; 530/387.1; 530/387.3; 514/44; 536/23.1
(58) Field of Search .................. 514/44; 435/320.1, 435/455, 325, 468; 536/23.1; 530/387.3, 387.1

(56) References Cited

U.S. PATENT DOCUMENTS

| 4,704,692 A | 11/1987 | Ladner |
| 4,881,175 A | 11/1989 | Ladner |
| 4,946,778 A | 8/1990 | Ladner et al. |
| 5,049,504 A | 9/1991 | Maugh et al. ......... 435/252.33 |
| 5,091,513 A | 2/1992 | Huston et al. |
| 5,166,320 A | 11/1992 | Wu et al. .................. 530/395 |
| 5,202,236 A | 4/1993 | Maugh et al. ............. 435/69.1 |
| 5,202,256 A | 4/1993 | Maugh et al. ............. 435/252.3 |
| 5,212,075 A | 5/1993 | Bednarski et al. |
| 5,258,498 A | 11/1993 | Huston et al. |
| 5,260,203 A | 11/1993 | Ladner et al. |
| 5,438,040 A | 8/1995 | Ekwuribe |
| 5,443,953 A | 8/1995 | Hansen et al. |
| 5,455,030 A | 10/1995 | Ladner et al. |
| 5,482,858 A | 1/1996 | Huston et al. |
| 5,518,889 A | 5/1996 | Ladner et al. |
| 5,521,291 A | 5/1996 | Curiel et al. |
| 5,534,254 A | 7/1996 | Huston et al. |
| 5,547,932 A | 8/1996 | Curiel et al. |
| 5,635,603 A | 6/1997 | Hansen et al. |
| 5,656,465 A | 8/1997 | Panicali et al. |
| 5,661,025 A | 8/1997 | Szoka, Jr. et al. |
| 5,714,350 A | 2/1998 | Co et al. |
| 5,753,204 A | 5/1998 | Huston et al. ............. 424/1.49 |
| 5,844,107 A | 12/1998 | Hanson et al. ............. 536/23.1 |
| 5,853,723 A | 12/1998 | Jacobs et al. |
| 5,856,456 A | 1/1999 | Whitlow et al. ........... 536/23.4 |
| 5,869,620 A | 2/1999 | Whitlow et al. |
| 5,872,222 A | 2/1999 | Chang |
| 5,888,773 A | 3/1999 | Jost et al. |
| 5,981,273 A | 11/1999 | Curiel et al. ............. 435/320.1 |
| 5,990,275 A | 11/1999 | Whitlow et al. |
| 5,998,144 A | 12/1999 | Reff et al. |
| 6,022,735 A | 2/2000 | Curiel et al. |
| 6,025,158 A | 2/2000 | Gonzalez et al. |
| 6,027,725 A | 2/2000 | Whitlow et al. ......... 424/136.1 |
| 6,077,663 A | 6/2000 | Curiel et al. |
| 6,143,520 A | * 11/2000 | Marasco et al. ........... 435/69.1 |
| 6,274,322 B1 | 8/2001 | Curiel et al. .................. 435/6 |
| 6,323,322 B1 | 11/2001 | Filpula et al. ........... 530/387.3 |

FOREIGN PATENT DOCUMENTS

| WO | WO 92/16555 | 10/1992 |
| WO | WO 93/11161 | 6/1993 |
| WO | WO 94/04691 | 3/1994 |
| WO | WO 94/12520 | 6/1994 |
| WO | WO 95/11020 | 4/1995 |
| WO | WO 96/09325 | 3/1996 |
| WO | WO 96/13599 | 5/1996 |
| WO | WO 96/23794 | 8/1996 |
| WO | WO 96/40731 | 12/1996 |
| WO | WO 97/14719 | 4/1997 |
| WO | WO 98/25971 | 6/1998 |
| WO | WO 98/48837 | 11/1998 |
| WO | WO 98/49198 | 11/1998 |
| WO | WO 99/64460 | 12/1999 |

OTHER PUBLICATIONS

Orkin, et al. Report and Recommendation of the Panel to Assess the NIH Investment in Research on Gene Therapy, The National Institutes of Health, Dec. 7, 1995.*
Verma, et al. Nature. Sep. 1997, vol. 389, pp. 239–242.*
Anderson, French W. Nature. Apr. 1998, vol. 392, pp. 25–30.*

(List continued on next page.)

Primary Examiner—Gerry Leffers
(74) Attorney, Agent, or Firm—Muserlian, Lucas & Mercanti, LLP

(57) ABSTRACT

The present invention is directed to a method of in vivo and ex vivo gene delivery, for a variety of cells. More specifically, it relates to a novel carrier system and method for targeted delivery of nucleic acids to mammalian cells. More specifically, the present invention relates to carrier system comprising single-chain polypeptide binding molecules having an a region rich in basic amino acid and having the three dimensional folding and, thus, the binding ability and specificity, of the variable region of an antibody. The basic amino acid rich region can comprise oligo-lysine, oligo-arginine or combinations thereof. Such preparations of modified single chain polypeptide binding molecules also have ability to bind nucleic acids at the region rich in basic amino acid residues. These properties of the modified single chain polypeptide binding molecules make them very useful in a variety of therapeutic applications including gene therapy. The invention also relates to multivalent antigen-binding molecules having regions rich in basic amino acids. Compositions of, genetic constructions for, methods of use, and methods for producing basic amino acid tailed antigen-binding proteins are disclosed.

16 Claims, 11 Drawing Sheets

OTHER PUBLICATIONS

Bogdanov Jr., A., et al., "Graft Copolymers as Carriers for Systemic Delivery of Expression Vectors," *Proceed. Intl. Symp. Control. Rel. Bioact. Mater.* 25:91–92, Controlled Release Society, Inc. (Jun. 1998).

Luo, D., et al., "An Engineered Bivalent Single–Chain Antibody Fragment That Increases Antigen Binding Activity," *J. Biochem* 121:831–834, Japanese Biochemical Society (May 1997).

Skerra, A., et al., "The Functional Expression of Antibody $F_v$ Fragments in *Escherichia coli*: Improved Vectors and a Generally Applicable Purification Technique," *Bio/Technol.* 9:273–278, Nature Publishing Company (1991).

Wadhwa, M.S., et al., "Peptide–Mediated Gene Delivery: Influence of Peptide Structure on Gene Expression," *Bioconjugate Chem.* 8:81–88, American Chemical Society (Jan. 1997).

Whitlow, M., et al., "An improved linker for single–chain Fv with reduced aggregation and enhanced proteolytic stability," *Protein Eng.* 6:989–995, Oxford University Press (1993).

Amit, A.G et al., "Three Dimensional Structure of an Antigen–Antibody Complex at 2.8 Å Resolution," *Science* 233:747–753, Association for the Advancement of Science (1986).

Benhar, I. et al., "Mutations of Two Lysine Residues in the CDR Loops of a Recombinant Immunotoxin That Reduce Its Sensitivity to Chemical Derivatization," *Bioconj. Chem.* 5:321–326, American Chemical Society (1994).

Bird, R.E. et al., "Single–Chain Antigen–Binding Proteins," *Science* 242:423–426, Association for the Advancement of Science (1988).

Co, M.S. et al., "Chimeric and Humanized Antibodies with Specificity for the CD33 Antigen," *J. Immunol.* 148:1149–1154, The American Association of Immunologists (1992).

DeLente, J.J., "Glycosylation revisited," *Trends in Biotechnol.* 3:218, Elsevier Science Publishers B.V. (1985).

Desplancq, D. et al., "Multimerization behavior of single chain Fv variants for the tumour–binding antibody B72.3," *Protein Engineering* 7:1027–1033, Oxford University Press (1994).

Eldin, P. et al., "High–level secretion of two antibody single chain Fv fragments by *Pichia pastoris*," *J. Immunol. Meth.* 201:67–75, Elsevier Science B.V. (Feb. 1997).

Filpula, D. et al., "Production of single–chain Fv monomers and multimers," in *Antibody Engineering: A Practical Approach*, McCafferty, J., et al., eds., IRL Press (Oxford University Press), Oxford, UK, pp. 253–268 (Aug. 1996).

Filpula, D., "PEGylated sFv and Glycosylated sFv," Part of Booklet distributed at: IBC's Eighth Annual International Conference on Antibody Engineering: New Technology, Application & Commercialization, Dec. 3, 1997.

Filpula, D., "PEGylated sFv and Glycosylated sFv," Slide Presentation at: IBC's Eighth Annual International Conference on Antibody Engineering: New Technology, Application & Commercialization, Dec. 3, 1997.

Filpula, D., "PEGylated sFv and Glycosylated sFv," Abstract from: IBC's Eighth Annual International Conference on Antibody Engineering: New Technology, Application & Commercialization, meeting date Dec. 3, 1997.

Gavel, Y. and G. von Heijne, "Sequence differences between glycosylated and non–glycosylated Asn–X–Thr/Ser acceptor sites: implications for protein engineering," *Protein Engineering* 3:433–442, Oxford University Press (1990).

Goodson, R.J. and N.V. Katre, "Site–Directed Pegylation of Recombinant Interleukin–2 at Its Glycosylation Site," *Bio/Technology* 8:343–346, Nature Publishing Co. (1990).

Greenman, J. et al., "The use of intracellular single–chain antibody fragments to inhibit specifically the expression of the cell surface molecules," *J. Immunol. Meth.* 194:169–180, Elsevier Science B.V. (Aug. 1996).

Greenwald, R.B., "Drug delivery systems: anticancer prodrugs and their polymeric conjugates," *Exp. Opin. Ther. Patents* 7:601–609, Ashley Publications Ltd. (Jun. 1997).

Hershfield, M.S. et al., "Use of site–directed mutagenesis to enhance the epitome–shielding effect of covalent modification of proteins with polyethylene glycol," *Proc. Natl. Acad. Sci. USA* 88:7185–7189, National Academy of Sciences of the USA (1991).

Hooftman, G. et al., "Review: Poly(ethylene glycol)s with Reactive Endgroups. II. Practical Consideration for the Preparation of Protein–PEG Conjugates," *J. Bioactive Compat. Polymers* 11:135–159, Technomic Publishing Co., Inc. (1996).

Huber, R., "Structural Basis for Antigen–Antibody Recognition," *Science* 233:702–703, American Association for the Advancement of Science (1986).

Jost, C.R., et al., "Mammalian Expression and Secretion of Functional Single–chain Fv Molecules," *J. Biol. Chem.* 269:26267–26273, American Society for Biochemistry and Molecular Biology, Inc. (1994).

Keck, P.C. and J.S. Huston, "Symmetry of Fv Architecture Is Conducive to Grafting a Second Antibody Binding Site in the Fv Region," *Biophys. J.* 71:2002–2011, Biophysical Society (Oct. 1996).

Leung, S.–o. et al., "Engineering a Unique Glycosylation Site for Site–Specific Conjugation of Haptens to Antibody Fragments," *J. Immunol.* 154:5919–5926, The American Association of Immunologists (1995).

Leung, S.–o. et al., "Effect of VK Framework–1 Glycosylation on the Binding Affinity of Lymphoma–Specific Murine and Chimeric LL2 Antibodies and Its Potential Use as a Novel Conjugation Site," *Int. J. Cancer* 60:534–538, Wiley–Liss, Inc. (1995).

Marasco, W.A. et al., "Simple Single–Chain Antibody Fusion Proteins as DNA Carriers," in: *IBC's Eighth Annual International Conference on Antibody Engineering: New Technology, Application & Commercialization*, Dec. 3–5, 1997, Hotel del Coronado, Coronado, CA, International Business Communications, 1 p. (Dec. 1997).

Marasco, W.A. et al., "Antibody–Mediated Gene Transfer into Human Hematopoietic Cells," in: *IBC's Seventh Annual International Conference on Antibody Engineering: New Technology, Application & Commercialization*, Dec. 2–4, 1996, Hotel del Coronado, Coronado, CA, International Business Communications, Session 1: Therapeutic Strategies, 1 p. (Dec. 1996).

Muyldermans, S. et al.. "Sequence and structure of $V_H$ domain from naturally occurring camel heavy chain immunoglobulins lacking light chains," *Protein Engin.* 7:1129–1135, Oxford University Press (1994).

Nathan, A. et al., "Copolymers of Lysine and Polyethylene Glycol: A New Family of Functionalized Drug Carriers," *Bioconj. Chem.* 4:54–62, American Chemical Society (1993).

Pai, L.H. et al., "Anti–tumor activities of immunotoxins made of monoclonal antibody B3 and various forms of Pseudomonas exotoxin," *Proc. Natl. Acad. Sci. USA* 88:3358–3362. National Academy of Sciences of the USA (1991).

Panka, D.J. et al., "Variable region framework differences result in decreased or increased affinity of variant anti–dioxin antibodies," *Proc. Natl. Acad. Sci. USA* 85:3080–3084, National Academy of Sciences of the USA (1988).

Plank, C. et al., "Branched Cationic Peptides for Gene Delivery: Role of Type and Number of Cationic Residues in Formation and in Vitro Activity of DNA Polyplexes," *Human Gene Ther.* 10:319–332, Mary Ann Liebert (Jan. 1999).

Prammer, K.V. and L. Otvos, Jr., "Structural Effects of Glycosylation on the C–Terminal Pentapeptide of Peptide T," *Biomedical Peptides, Proteins & Nucl. Acids* 1:221–226, Mayflower Worldwide Ltd. (1995).

Reiter, Y. et al., "Engineering antibody Fv fragments for cancer detection and therapy: Disulfide–stabilized Fv fragments," *Nature Biotechnology* 14:1239–1245, Nature Publishing Co. (Oct. 1996).

Ridder, R. et al.. "Generation of Rabbit Monoclonal Antibody Fragments from a Combinatorial Phage Display Library and Their Production in the Yeast *Pichia pastoris*," *Bio/Technology* 13:255–260, Nature Publishing Co. (1995).

Rudikoff, S. et al., "Single amino acid substitution altering antigen–binding specificity," *Proc. Natl. Acad. Sci. USA* 79:1979–1983, National Academy of Sciences of the USA (1982).

Schaffhausen, B.S., "Chapter 21. Designing and Using Site–Specific Antibodies to Synthetic Peptides," in: *Hybridoma Technology in the Biosciences and Medicine*, Springer, T.A., ed., Plenum Press, NY, pp. 355–373 (1985).

Sela, M. and E. Hurwitz, "Chapter 10. Conjugates of Antibodies with Cytotoxic Drugs," in: *Immunoconjugates. Antibody Conjugates in Radioimaging and Therapy of Cancer*, Vogel, C.–W., ed., Oxford University Press, New York, NY, pp. 189–195 (1987).

Verhaar, M.J. et al., "Technetium–99m Radiolabeling Using a Phage–Derived Single–Chain Fv with a C–Terminal Cysteine," *J. Nucl. Med.* 37:868–872, Society of Nucler Medicine, Inc. (May 1996).

Wang, M. et al., "Single–chain Fv with manifold N–glycans as bifunctional scaffolds for immunomolecules," *Prot. Eng.* 11:1277–1283, Oxford University Press (Dec. 1998).

Wang, Q.–c. et al., "Polyethylene Glycol–modified Chimeric Toxin Composed of Transforming Growth Factor α and Pseudomonas Exotoxin," *Cancer Res.* 53:4588–4594, American Association for Cancer Research (1993).

Whitlow, M. et al., "1.85 Å structure of anti–fluorescein 4–4–20 Fab," *Protein Engineering* 8:749–761 (1995).

Wright, A. et al., "Antibody variable region glycosylation: position effects on antigen binding and carbohydrate structure," *EMBO J.* 10:2717–2723, Oxford University Press (1991).

Wright, A. and S.L. Morrison, "Antibody variable region glycosylation: biochemical and clinical effects," *Springer Semin. Immunopathol.* 15:259–273, Springer–Verlag (1993).

Zalipsky, S. et al., "Chemistry of polyethylene glycol conjugates with biologically active molecules," *Adv. Drug Del. Res.* 16:157–182, Elsevier Science B.V. (1995).

Zalipsky, S., "Functionalized Poly(ethylene glycol) for Preparation of Biologically Relevant Conjugates," *Bioconj. Chem.* 6:150–165, American Chemical Society (1995).

Fahnestock, S.R. and Irwin, S.L., "Synthetic spider dragline silk proteins and their production in *Escherichia coli*," *Appl. Microbiol. Biotechnol.* 47:23–32, Springer–Verlag (Jan. 1997).

Anand, N.N. et al., "Bacterial Expression and Secretion of Various Single–chain Fv Genes Encoding Proteins Specific for a Salmonella Serotype B O–Antigen," *J. Biol. Chem.* 266:21874–21879, The American Society for Biochemistry and Molecular Biology, Inc. (1991).

Avrameas, A. et al., "Polyreactive anti–DNA monoclonal antibodies and a derived peptide as vectors for the intracytoplasmic and intranuclear translocation of macromolecules," *Proc. Natl. Acad. Sci. USA* 95:5601–5606, National Academy of Sciences (May 1998).

Chen, S.–Y. et al., "Design of a genetic immunotoxin to eliminate toxin immunogenicity," *Gene Ther.* 2:116–123, Stockton Press (1995).

Colcher, D. et al., "In Vivo Tumor Targeting of a Recombinant Single–Chain Antigen–Binding Protein," *J. Natl. Cancer Inst.* 82:1191–1197, Oxford university Press (1990).

Cumber, A.J. et al., "Comparative Stabilities In Vitro and In Vivo of a Recombinant Mouse Antibody FvCys Fragment and A bisFvCys Conjugate," *J. Immunol.* 149:120–126, The American Association of Immunologists (1992).

Fominaya, J. and W. Wels, "Target Cell–specific DNA Transfer Mediated by a Chimeric Multidomain Protein," *J. Biol. Chem.* 271:10560–10568, The American Society for Biochemistry and Molecular Biology, Inc. (1996).

George, A.J.T. et al., "Production of a Bispecific Antibody by Linkage of Two Recombinant Single Chain Fv Molecules," *J. Cell. Biochem. Suppl.* 15E:127, Abstract No. N 206, Wiley–Liss (1991).

Hämmerling, G.J. et al., "Appendix. Production of Antibody–Producing Hybridomas in the Rodent Systems," in *Monoclonal Antibodies and T–Cell Hybridomas*, Hämmerling, G.J. et al., eds., Elsevier/North–Holland Biomedical Press, Amsterdam, The Netherlands, pp. 563–587 (1981).

Holliger, P. et al., " 'Diabodies': Small bivalent and bispecific antibody fragments," *Proc. Natl. Acad. Sci. USA* 90:6444–6448, National Academy of Sciences (1993).

Hoogenboom, H.R., "Mix and match: Building manifold binding sites," *Nature Biotechnol.* 15:125–126, Nature Publishing Company (Feb. 1997).

Köhler, G. and C. Milstein, "Continuous cultures of fused cells secreting antibody of predefined specificity," *Nature* 256:495–497, MacMillan Journals Ltd. (1975).

Köhler, G. et al., "Fusion between immunoglobulin–secreting and nonsecreting myeloma cell lines," *Eur. J. Immunol.* 6:292–295, Verlag Chemie GmbH (1976).

Köhler, G. and C. Milstein, "Derivation of specific antibody–producing tissue culture and tumor lines by cell fusion," *Eur. J. Immunol.* 6:511–519, Verlag Chemie GmbH (1976).

Milenic, D.E. et al., "Construction, Binding Properties, Metabolism, and Tumor Targeting of a Single–Chain Fv Derived from the Pancarcinoma Monoclonal Antibody CC49," *Cancer Res.* 51:6363–6371, American Association for Cancer Research (1991).

Pardridge, W.M. et al., "Enhanced Endocytosis in Cultured Human Breast Carcinoma Cells and In Vivo Biodistribution in Rats of a Humanized Monoclonal Antibody after Cationization of the Protein," *J. Pharmacol. & Exper. Therapeut.* 286:548–554, American Society for Pharmacology and Experimental Therapeutics (Jul. 1998).

Robinson, P. et al., "Effect of Polyethylene Glycol Conjugated to DNA–Transfecting Complexes Targeted at the Transferrin Receptor of HeLa Cells," *Drug Delivery* 4:115–119, Taylor & Francis (Apr. 1997).

Whitlow, M. and D. Filpula, "Single–Chain Fv Proteins and Their Fusion Proteins," *Methods: A Companion to Methods in Enzymology* 2:97–105, Academic press, Inc. (1991).

Whitlow, M. et al., "Multivalent Fvs: characterization of single–chain Fv oligomers and preparation of a bispecific Fv," *Protein Eng.* 7:1017–1026, Oxford University Press (1994).

Yokota, T. et al., "Rapid Tumor Penetration of a Single–Chain Fv and Comparison with Other Immunoglobulin Forms," *Cancer Res.* 52:3402–3408, American Association for Cancer Research (1992).

* cited by examiner

```
CC49 V_L                                      12            15
  D   V   V   M   S   Q   S   P   S   S   L   P   V   S   V
 GAC GTC GTG ATG TCA CAG TCT CCA TCC TCC CTA CCT GTG TCA GTT
 Aat II                                                    27C
  G   E   K   V   T   L   S   C   K   S   S   Q   S   L   L
 GGC GAG AAG GTT ACT TTG AGC TGC AAG TCC AGT CAG AGC CTT TTA
                                                            39
  Y   S   G   N   Q   K   N   Y   L   A   W   Y   Q   Q   K
 TAT AGT GGT AAT CAA AAG AAC TAC TTG GCC TGG TAC CAG CAG AAA
                                                            54
  P   G   Q   S   P   K   L   L   I   Y   W   A   S   A   R
 CCA GGG CAG TCT CCT AAA CTG CTG ATT TAC TGG GCA TCC GCT AGG
                                                            69
  E   S   G   V   P   D   R   F   T   G   S   G   S   G   T
 GAA TCT GGG GTC CCT GAT CGC TTC ACA GGC AGT GGA TCT GGG ACA
                        77                                  84
  D   F   T   L   S   I   S   S   V   K   T   E   D   L   A
 GAT TTC ACT CTC TCC ATC AGC AGT GTG AAG ACT GAA GAC CTG GCA
                                                            99
  V   Y   Y   C   Q   Q   Y   Y   S   Y   P   L   T   F   G
 GTT TAT TAC TGT CAG CAG TAT TAT AGC TAT CCC CTC ACG TTC GGT

218 Linker
  A   G   T   K   L   V   L   K   G   S   T   S   G   S   G
 GCT GGG ACC AAG CTT GTG CTG AAA GGC TCT ACT TCC GGT AGC GGC
             Hind III
                                           CC49 V_H     4
  K   P   G   S   G   E   G   S   T   K   G   Q   V   Q   L
 AAA CCC GGG AGT GGT GAA GGT AGC ACT AAA GGT CAG GTT CAG CTG
     Sma I                                          Pvu II
                                    13                      19
  Q   Q   S   D   A   E   L   V   K   P   G   A   S   V   K
 CAG CAG TCT GAC GCT GAG TTG GTA AAA CCT GGG GCT TCA GTG AAG
                                                            34
  I   S   C   K   A   S   G   Y   T   F   T   D   H   A   I
 ATT TCC TGC AAG GCT TCT GGC TAC ACC TTC ACT GAC CAT GCA ATT
                                                            49
  H   W   V   K   Q   N   P   E   Q   G   L   E   W   I   G
 CAC TGG GTG AAA CAG AAC CCT GAA CAG GGC CTG GAA TGG ATT GGA
                                                            63
  Y   F   S   P   G   N   D   D   F   K   Y   N   E   R   F
 TAT TTT TCT CCC GGA AAT GAT GAT TTT AAA TAC AAT GAG AGG TTC
                                                            78
  K   G   K   A   T   L   T   A   D   K   S   S   S   T   A
 AAG GGC AAG GCC ACA CTG ACT GCA GAC AAA TCC TCC AGC ACT GCC
                 82B                                        90
  Y   V   Q   L   N   S   L   T   S   E   D   S   A   V   Y
 TAC GTG CAG CTC AAC AGC CTG ACA TCT GAG GAT TCT GCA GTG TAT
                                                           107
  F   C   T   R   S   L   N   M   A   Y   W   G   Q   G   T
 TTC TGT ACA AGA TCC CTG AAT ATG GCC TAC TGG GGT CAA GGA ACC
                    112
  S   V   T   V   S   K   K   K   K   K   K   K   K   V   T
 TCG GTC ACC GTC TCC AAA AAG AAG AAA AAA AAG AAA AAG GTC ACC
     BstEII          *   *   *   *   *   *   *   * BstEII V   S
 GTC TCC TAA TAGGATCC
              BamHI
```

```
                                             12              15
 D   V   V   M   S   Q   S   P   S   S   L   P   V   S   V
GAC GTC GTG ATG TCA CAG TCT CCA TCC TCC CTA CCT GTG TCA GTT
Aat II                                                   27C
 G   E   K   V   T   L   S   C   K   S   S   Q   S   L   L
GGC GAG AAG GTT ACT TTG AGC TGC AAG TCC AGT CAG AGC CTT TTA
                                                          39
 Y   S   G   N   Q   K   N   Y   L   A   W   Y   Q   Q   K
TAT AGT GGT AAT CAA AAG AAC TAC TTG GCC TGG TAC CAG CAG AAA
                                                          54
 P   G   Q   S   P   K   L   L   I   Y   W   A   S   A   R
CCA GGG CAG TCT CCT AAA CTG CTG ATT TAC TGG GCA TCC GCT AGG
                                                          69
 E   S   G   V   P   D   R   F   T   G   S   G   S   G   T
GAA TCT GGG GTC CCT GAT CGC TTC ACA GGC AGT GGA TCT GGG ACA
                         77                               84
 D   F   T   L   S   I   S   S   V   K   T   E   D   L   A
GAT TTC ACT CTC TCC ATC AGT AGT GTG AAG ACT GAA GAC CTG GCA
                                                          99
 V   Y   Y   C   Q   Q   Y   Y   S   Y   P   L   T   F   G
GTT TAT TAC TGT CAG CAG TAT TAT AGC TAT CCC CTC ACG TTC GGT
                                    218 Linker
 A   G   T   K   L   V   L   K   G   S   T   S   G   S   G
GCT GGG ACC AAG CTT GTG CTG AAA GGC TCT ACT TCC GGT AGC GGC
             Hind III
                                        CC49 V$_H$    4
 K   P   G   S   G   E   G   S   T   K   G   Q   V   Q   L
AAA CCC GGG AGT GGT GAA GGT AGC ACT AAA GGT CAG GTT CAG CTG
     Sma I                                        Pvu II 13                   19
 Q   Q   S   D   A   E   L   V   K   P   G   A   S   V   K
CAG CAG TCT GAC GCT GAG TTG GTG AAA CCT GGG GCT TCA GTG AAG
                                                          34
 I   S   C   K   A   S   G   Y   T   F   T   D   H   A   I
ATT TCC TGC AAG GCT TCT GGC TAC ACC TTC ACT GAC CAT GCA ATT
```

FIG.2A

```
                                                              49
      H    W    V    K    Q    N    P    E    Q    G    L    E    W    I    G
     CAC  TGG  GTG  AAA  CAG  AAC  CCT  GAA  CAG  GGC  CTG  GAA  TGG  ATT  GGA
                                                                            63
      Y    F    S    P    G    N    D    D    F    K    Y    N    E    R    F
     TAT  TTT  TCT  CCC  GGA  AAT  GAT  GAT  TTT  AAA  TAC  AAT  GAG  AGG  TTC
                                                                            78
      K    G    K    A    T    L    T    A    D    K    S    S    S    T    A
     AAG  GGC  AAG  GCC  ACA  CTG  ACT  GCA  GAC  AAA  TCC  TCC  AGC  ACT  GCC
                              82B                                           90
      Y    V    Q    L    N    S    L    T    S    E    D    S    A    V    Y
     TAC  GTG  CAG  CTC  AAC  AGC  CTG  ACA  TCT  GAG  GAT  TCT  GCA  GTG  TAT
                                                                           107
      F    C    T    R    S    L    N    M    A    Y    W    G    Q    G    T
     TTC  TGT  ACA  AGA  TCC  CTG  AAT  ATG  GCC  TAC  TGG  GGT  CAA  GGA  ACC
                              112
      S    V    T    V    S    K    K    K    K    K    K    K    V    T
     TCG  GTC  ACC  GTC  TCC  AAA  AAG  AAG  AAA  AAA  AAG  AAA  AAG  GTC  ACC
     BstEII                    *    *    *    *    *    *    *    *  BstEII

V    S    K    K    K    K    K    K    K    V    T    V    S
     GTC  TCC  AAA  AAG  AAG  AAA  AAA  AAG  AAA  AAG  GTC  ACC  GTC  TCC  TAA
                 *    *    *    *    *    *    *    *  BstEII

TAGGATCC
        BamHI
```

FIG.2B

A33/218 sFv with Engineered 16 lysine tail

A33 V_L

```
                        12                        20
D V V M T Q S Q K F M S T S V G D R V S

40
I T C K A S Q N V R T V V A W Y Q Q K P
      ─────────────────────

60
G Q S P K T L I Y L A S N R H T G V P D
                  ───────────────

77
R F T G S G S G T D F T L T I S N V Q S

100
E D L A D Y F C L Q H W S Y P L T F G S
                ═══════════════
```

218 Linker

Kabat Consensus V$_K$I / 218 / V$_H$III sFv with Engineered 16 Lysine Tail

V$_L$ (V$_K$I)

```
                        12                              22
D  I  Q  M  T  Q  S  P  S  S  L  S  A  S  V  G  D  R  V  T  I  T

41
C  R  A  S  Q  S  L  V  S  I  S  N  Y  L  A  W  Y  Q  Q  K  P  G

63
K  A  P  K  L  L  I  Y  A  A  S  S  L  E  S  G  V  P  S  R  F  S 77                              85
G  S  G  S  G  T  D  F  T  L  T  I  S  S  L  Q  P  E  D  F  A  T

106
Y  Y  C  Q  Q  Y  N  S  L  P  E  W  T  F  G  Q  G  T  K  V  E  I
```

218 Linker                                                                V$_H$ (V$_H$III)

C6.5/218 sFv with Engineered 16 Lysine Tail

C6.5 V_L

```
                        12                                              23
Q  S  V  L  T  Q  P  P  S  V  S  A  A  P  G  Q  K  V  T  I  S  C

43
S  G  S  S  S  N  I  G  N  N  Y  V  S  W  Y  Q  Q  L  P  G  T  A

65
P  K  L  L  I  Y  G  H  T  N  R  P  A  G  V  P  D  R  F  S  G  S 77                                      87
K  S  G  T  S  A  S  L  A  I  S  G  F  R  S  E  D  E  A  D  Y  Y

106A
C  A  A  W  D  D  S  L  S  G  W  V  F  G  G  G  T  K  L  T  V  L
```

C6.5 V_H
218 Linker                                                 3

SEQUENCE LISTING

<160> NUMBER OF SEQ ID NOS: 13

<210> SEQ ID NO 1
<211> LENGTH: 782
<212> TYPE: DNA
<213> ORGANISM: Artificial Sequence
<220> FEATURE:
<223> OTHER INFORMATION: Description of Artificial Sequence: CC49/218 sFv
<221> NAME/KEY: CDS
<222> LOCATION: (1)..(771)

<400> SEQUENCE: 1

```
gac gtc gtg atg tca cag tct cca tcc tcc cta cct gtg tca gtt ggc      48
Asp Val Val Met Ser Gln Ser Pro Ser Ser Leu Pro Val Ser Val Gly
 1               5                  10                  15 gag aag gtt act ttg agc tgc aag tcc agt cag agc ctt tta tat agt      96
Glu Lys Val Thr Leu Ser Cys Lys Ser Ser Gln Ser Leu Leu Tyr Ser
             20                  25                  30 ggt aat caa aag aac tac ttg gcc tgg tac cag cag aaa cca ggg cag     144
Gly Asn Gln Lys Asn Tyr Leu Ala Trp Tyr Gln Gln Lys Pro Gly Gln
         35                  40                  45 tct cct aaa ctg ctg att tac tgg gca tcc gct agg gaa tct ggg gtc     192
Ser Pro Lys Leu Leu Ile Tyr Trp Ala Ser Ala Arg Glu Ser Gly Val
     50                  55                  60 cct gat cgc ttc aca ggc agt gga tct ggg aca gat ttc act ctc tcc     240
Pro Asp Arg Phe Thr Gly Ser Gly Ser Gly Thr Asp Phe Thr Leu Ser
 65                  70                  75                  80 atc agc agt gtg aag act gaa gac ctg gca gtt tat tac tgt cag cag     288
Ile Ser Ser Val Lys Thr Glu Asp Leu Ala Val Tyr Tyr Cys Gln Gln
                 85                  90                  95 tat tat agc tat ccc ctc acg ttc ggt gct ggg acc aag ctt gtg ctg     336
Tyr Tyr Ser Tyr Pro Leu Thr Phe Gly Ala Gly Thr Lys Leu Val Leu
            100                 105                 110 aaa ggc tct act tcc ggt agc ggc aaa ccc ggg agt ggt gaa ggt agc     384
Lys Gly Ser Thr Ser Gly Ser Gly Lys Pro Gly Ser Gly Glu Gly Ser
        115                 120                 125 act aaa ggt cag gtt cag ctg cag cag tct gac gct gag ttg gtg aaa     432
Thr Lys Gly Gln Val Gln Leu Gln Gln Ser Asp Ala Glu Leu Val Lys
    130                 135                 140 cct ggg gct tca gtg aag att tcc tgc aag gct tct ggc tac acc ttc     480
Pro Gly Ala Ser Val Lys Ile Ser Cys Lys Ala Ser Gly Tyr Thr Phe
145                 150                 155                 160 act gac cat gca att cac tgg gtg aaa cag aac cct gaa cag ggc ctg     528
Thr Asp His Ala Ile His Trp Val Lys Gln Asn Pro Glu Gln Gly Leu
                165                 170                 175 gaa tgg att gga tat ttt tct ccc gga aat gat gat ttt aaa tac aat     576
Glu Trp Ile Gly Tyr Phe Ser Pro Gly Asn Asp Asp Phe Lys Tyr Asn
            180                 185                 190 gag agg ttc aag ggc aag gcc aca ctg act gca gac aaa tcc tcc agc     624
Glu Arg Phe Lys Gly Lys Ala Thr Leu Thr Ala Asp Lys Ser Ser Ser
        195                 200                 205 act gcc tac gtg cag ctc aac agc ctg aca tct gag gat tct gca gtg     672
Thr Ala Tyr Val Gln Leu Asn Ser Leu Thr Ser Glu Asp Ser Ala Val
```

```
                     210                 215                 220
tat ttc tgt aca aga tcc ctg aat atg gcc tac tgg ggt caa gga acc      720
Tyr Phe Cys Thr Arg Ser Leu Asn Met Ala Tyr Trp Gly Gln Gly Thr
225                 230                 235                 240 tcg gtc acc gtc tcc aaa aag aag aaa aaa aag aaa aag gtc acc gtc      768
Ser Val Thr Val Ser Lys Lys Lys Lys Lys Lys Lys Lys Val Thr Val
                245                 250                 255 tcc taataggatc c                                                     782
Ser
```

<210> SEQ ID NO 2
<211> LENGTH: 257
<212> TYPE: PRT
<213> ORGANISM: Artificial Sequence
<220> FEATURE:
<223> OTHER INFORMATION: Description of Artificial Sequence: CC49/218 sFv

<400> SEQUENCE: 2

```
Asp Val Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Ala Arg Glu Ser Gly Val
        50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Gly Ser Thr Ser Gly Ser Gly Lys Pro Gly Ser Gly Glu Gly Ser
        115                 120                 125

Thr Lys Gly Gln Val Gln Leu Gln Gln Ser Asp Ala Glu Leu Val Lys
130                 135                 140

Pro Gly Ala Ser Val Lys Ile Ser Cys Lys Ala Ser Gly Tyr Thr Phe
145                 150                 155                 160

Thr Asp His Ala Ile His Trp Val Lys Gln Asn Pro Glu Gln Gly Leu
                165                 170                 175

Glu Trp Ile Gly Tyr Phe Ser Pro Gly Asn Asp Asp Phe Lys Tyr Asn
            180                 185                 190

Glu Arg Phe Lys Gly Lys Ala Thr Leu Thr Ala Asp Lys Ser Ser Ser
        195                 200                 205

Thr Ala Tyr Val Gln Leu Asn Ser Leu Thr Ser Glu Asp Ser Ala Val
210                 215                 220

Tyr Phe Cys Thr Arg Ser Leu Asn Met Ala Tyr Trp Gly Gln Gly Thr
225                 230                 235                 240

Ser Val Thr Val Ser Lys Lys Lys Lys Lys Lys Lys Val Thr Val
                245                 250                 255

Ser
```

<210> SEQ ID NO 3
<211> LENGTH: 818
<212> TYPE: DNA
<213> ORGANISM: Artificial Sequence -continued

```
<220> FEATURE:
<223> OTHER INFORMATION: Description of Artificial Sequence: CC49/218
      sFv
<221> NAME/KEY: CDS
<222> LOCATION: (1)..(807)

<400> SEQUENCE: 3 gac gtc gtg atg tca cag tct cca tcc tcc cta cct gtg tca gtt ggc      48
Asp Val Val Met Ser Gln Ser Pro Ser Ser Leu Pro Val Ser Val Gly
 1               5                  10                  15 gag aag gtt act ttg agc tgc aag tcc agt cag agc ctt tta tat agt      96
Glu Lys Val Thr Leu Ser Cys Lys Ser Ser Gln Ser Leu Leu Tyr Ser
             20                  25                  30 ggt aat caa aag aac tac ttg gcc tgg tac cag cag aaa cca ggg cag     144
Gly Asn Gln Lys Asn Tyr Leu Ala Trp Tyr Gln Gln Lys Pro Gly Gln
         35                  40                  45 tct cct aaa ctg ctg att tac tgg gca tcc gct agg gaa tct ggg gtc     192
Ser Pro Lys Leu Leu Ile Tyr Trp Ala Ser Ala Arg Glu Ser Gly Val
     50                  55                  60 cct gat cgc ttc aca ggc agt gga tct ggg aca gat ttc act ctc tcc     240
Pro Asp Arg Phe Thr Gly Ser Gly Ser Gly Thr Asp Phe Thr Leu Ser
 65                  70                  75                  80 atc agc agt gtg aag act gaa gac ctg gca gtt tat tac tgt cag cag     288
Ile Ser Ser Val Lys Thr Glu Asp Leu Ala Val Tyr Tyr Cys Gln Gln
                 85                  90                  95 tat tat agc tat ccc ctc acg ttc ggt gct ggg acc aag ctt gtg ctg     336
Tyr Tyr Ser Tyr Pro Leu Thr Phe Gly Ala Gly Thr Lys Leu Val Leu
            100                 105                 110 aaa ggc tct act tcc ggt agc ggc aaa ccc ggg agt ggt gaa ggt agc     384
Lys Gly Ser Thr Ser Gly Ser Gly Lys Pro Gly Ser Gly Glu Gly Ser
        115                 120                 125 act aaa ggt cag gtt cag ctg cag cag tct gac gct gag ttg gtg aaa     432
Thr Lys Gly Gln Val Gln Leu Gln Gln Ser Asp Ala Glu Leu Val Lys
    130                 135                 140 cct ggg gct tca gtg aag att tcc tgc aag gct tct ggc tac acc ttc     480
Pro Gly Ala Ser Val Lys Ile Ser Cys Lys Ala Ser Gly Tyr Thr Phe
145                 150                 155                 160 act gac cat gca att cac tgg gtg aaa cag aac cct gaa cag ggc ctg     528
Thr Asp His Ala Ile His Trp Val Lys Gln Asn Pro Glu Gln Gly Leu
                165                 170                 175 gaa tgg att gga tat ttt tct ccc gga aat gat gat ttt aaa tac aat     576
Glu Trp Ile Gly Tyr Phe Ser Pro Gly Asn Asp Asp Phe Lys Tyr Asn
            180                 185                 190 gag agg ttc aag ggc aag gcc aca ctg act gca gac aaa tcc tcc agc     624
Glu Arg Phe Lys Gly Lys Ala Thr Leu Thr Ala Asp Lys Ser Ser Ser
        195                 200                 205 act gcc tac gtg cag ctc aac agc ctg aca tct gag gat tct gca gtg     672
Thr Ala Tyr Val Gln Leu Asn Ser Leu Thr Ser Glu Asp Ser Ala Val
    210                 215                 220 tat ttc tgt aca aga tcc ctg aat atg gcc tac tgg ggt caa gga acc     720
Tyr Phe Cys Thr Arg Ser Leu Asn Met Ala Tyr Trp Gly Gln Gly Thr
225                 230                 235                 240 tcg gtc acc gtc tcc aaa aag aag aaa aaa aag aaa aag gtc acc gtc     768
Ser Val Thr Val Ser Lys Lys Lys Lys Lys Lys Lys Lys Val Thr Val
                245                 250                 255 tcc aaa aag aag aaa aaa aag aaa aag gtc acc gtc tcc taataggatc c    818
Ser Lys Lys Lys Lys Lys Lys Lys Lys Val Thr Val Ser
            260                 265

<210> SEQ ID NO 4
<211> LENGTH: 269
```

```
<212> TYPE: PRT
<213> ORGANISM: Artificial Sequence
<220> FEATURE:
<223> OTHER INFORMATION: Description of Artificial Sequence: CC49/218
      sFv

<400> SEQUENCE: 4
```

| Asp | Val | Val | Met | Ser | Gln | Ser | Pro | Ser | Ser | Leu | Pro | Val | Ser | Val | Gly |
|---|---|---|---|---|---|---|---|---|---|---|---|---|---|---|---|
| 1 | | | | 5 | | | | | 10 | | | | | 15 | |

| Glu | Lys | Val | Thr | Leu | Ser | Cys | Lys | Ser | Ser | Gln | Ser | Leu | Leu | Tyr | Ser |
|---|---|---|---|---|---|---|---|---|---|---|---|---|---|---|---|
| | | | 20 | | | | | 25 | | | | | 30 | | |

| Gly | Asn | Gln | Lys | Asn | Tyr | Leu | Ala | Trp | Tyr | Gln | Lys | Pro | Gly | Gln |
|---|---|---|---|---|---|---|---|---|---|---|---|---|---|---|
| | | 35 | | | | | 40 | | | | | 45 | | |

| Ser | Pro | Lys | Leu | Leu | Ile | Tyr | Trp | Ala | Ser | Ala | Arg | Glu | Ser | Gly | Val |
|---|---|---|---|---|---|---|---|---|---|---|---|---|---|---|---|
| | 50 | | | | | 55 | | | | | 60 | | | | |

| Pro | Asp | Arg | Phe | Thr | Gly | Ser | Gly | Ser | Gly | Thr | Asp | Phe | Thr | Leu | Ser |
|---|---|---|---|---|---|---|---|---|---|---|---|---|---|---|---|
| 65 | | | | | 70 | | | | | 75 | | | | | 80 |

| Ile | Ser | Ser | Val | Lys | Thr | Glu | Asp | Leu | Ala | Val | Tyr | Tyr | Cys | Gln | Gln |
|---|---|---|---|---|---|---|---|---|---|---|---|---|---|---|---|
| | | | | 85 | | | | | 90 | | | | | 95 | |

| Tyr | Tyr | Ser | Tyr | Pro | Leu | Thr | Phe | Gly | Ala | Gly | Thr | Lys | Leu | Val | Leu |
|---|---|---|---|---|---|---|---|---|---|---|---|---|---|---|---|
| | | | 100 | | | | | 105 | | | | | 110 | | |

| Lys | Gly | Ser | Thr | Ser | Gly | Ser | Gly | Lys | Pro | Gly | Ser | Gly | Glu | Gly | Ser |
|---|---|---|---|---|---|---|---|---|---|---|---|---|---|---|---|
| | | | 115 | | | | | 120 | | | | | 125 | | |

| Thr | Lys | Gly | Gln | Val | Gln | Leu | Gln | Gln | Ser | Asp | Ala | Glu | Leu | Val | Lys |
|---|---|---|---|---|---|---|---|---|---|---|---|---|---|---|---|
| | 130 | | | | | 135 | | | | | 140 | | | | |

| Pro | Gly | Ala | Ser | Val | Lys | Ile | Ser | Cys | Lys | Ala | Ser | Gly | Tyr | Thr | Phe |
|---|---|---|---|---|---|---|---|---|---|---|---|---|---|---|---|
| 145 | | | | | 150 | | | | | 155 | | | | | 160 |

| Thr | Asp | His | Ala | Ile | His | Trp | Val | Lys | Gln | Asn | Pro | Glu | Gln | Gly | Leu |
|---|---|---|---|---|---|---|---|---|---|---|---|---|---|---|---|
| | | | | 165 | | | | | 170 | | | | | 175 | |

| Glu | Trp | Ile | Gly | Tyr | Phe | Ser | Pro | Gly | Asn | Asp | Asp | Phe | Lys | Tyr | Asn |
|---|---|---|---|---|---|---|---|---|---|---|---|---|---|---|---|
| | | | 180 | | | | | 185 | | | | | 190 | | |

| Glu | Arg | Phe | Lys | Gly | Lys | Ala | Thr | Leu | Thr | Ala | Asp | Lys | Ser | Ser | Ser |
|---|---|---|---|---|---|---|---|---|---|---|---|---|---|---|---|
| | | 195 | | | | | 200 | | | | | 205 | | | |

| Thr | Ala | Tyr | Val | Gln | Leu | Asn | Ser | Leu | Thr | Ser | Glu | Asp | Ser | Ala | Val |
|---|---|---|---|---|---|---|---|---|---|---|---|---|---|---|---|
| | 210 | | | | | 215 | | | | | 220 | | | | |

| Tyr | Phe | Cys | Thr | Arg | Ser | Leu | Asn | Met | Ala | Tyr | Trp | Gly | Gln | Gly | Thr |
|---|---|---|---|---|---|---|---|---|---|---|---|---|---|---|---|
| 225 | | | | | 230 | | | | | 235 | | | | | 240 |

| Ser | Val | Thr | Val | Ser | Lys | Lys | Lys | Lys | Lys | Lys | Val | Thr | Val |
|---|---|---|---|---|---|---|---|---|---|---|---|---|---|
| | | | | 245 | | | | | 250 | | | | 255 |

| Ser | Lys | Lys | Lys | Lys | Lys | Lys | Val | Thr | Val | Ser |
|---|---|---|---|---|---|---|---|---|---|---|
| | | | 260 | | | | | 265 | | |

```
<210> SEQ ID NO 5
<211> LENGTH: 265
<212> TYPE: PRT
<213> ORGANISM: Artificial Sequence
<220> FEATURE:
<223> OTHER INFORMATION: Description of Artificial Sequence: A33/218
      sFv

<400> SEQUENCE: 5
```

| Asp | Val | Val | Met | Thr | Gln | Ser | Gln | Lys | Phe | Met | Ser | Thr | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Ser | Ile | Thr | Cys | Lys | Ala | Ser | Gln | Asn | Val | Arg | Thr | Val |
|---|---|---|---|---|---|---|---|---|---|---|---|---|---|---|---|
| | | | 20 | | | | | 25 | | | | | 30 | | |

| Val | Ala | Trp | Tyr | Gln | Gln | Lys | Pro | Gly | Gln | Ser | Pro | Lys | Thr | Leu | Ile |
|---|---|---|---|---|---|---|---|---|---|---|---|---|---|---|---|
| | | | 35 | | | | | 40 | | | | | 45 | | |

```
Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Ser Tyr Pro Leu
                85                  90                  95

Thr Phe Gly Ser Gly Thr Lys Leu Glu Val Lys Gly Ser Thr Ser Gly
            100                 105                 110

Ser Gly Lys Pro Gly Ser Gly Glu Gly Ser Thr Lys Gly Glu Val Lys
            115                 120                 125

Leu Val Glu Ser Gly Gly Gly Leu Val Lys Pro Gly Gly Ser Leu Lys
    130                 135                 140

Leu Ser Cys Ala Ala Ser Gly Phe Ala Phe Ser Thr Tyr Asp Met Ser
145                 150                 155                 160

Trp Val Arg Gln Thr Pro Glu Lys Arg Leu Glu Trp Val Ala Thr Ile
                165                 170                 175

Ser Ser Gly Gly Ser Tyr Thr Tyr Tyr Leu Asp Ser Val Lys Gly Arg
            180                 185                 190

Phe Thr Ile Ser Arg Asp Ser Ala Arg Asn Thr Leu Tyr Leu Gln Met
            195                 200                 205

Ser Ser Leu Arg Ser Glu Asp Thr Ala Leu Tyr Tyr Cys Ala Pro Thr
    210                 215                 220

Thr Val Val Pro Phe Ala Tyr Trp Gly Gln Gly Thr Leu Val Thr Val
225                 230                 235                 240

Ser Lys Lys Lys Lys Lys Lys Lys Val Thr Val Ser Lys Lys Lys
                245                 250                 255

Lys Lys Lys Lys Lys Val Thr Val Ser
            260                 265

<210> SEQ ID NO 6
<211> LENGTH: 283
<212> TYPE: PRT
<213> ORGANISM: Artificial Sequence
<220> FEATURE:
<223> OTHER INFORMATION: Description of Artificial Sequence: Kabat
      Consensus
<221> NAME/KEY: UNSURE
<222> LOCATION: (232)
<223> OTHER INFORMATION: May be any amino acid.
<221> NAME/KEY: UNSURE
<222> LOCATION: (234)
<223> OTHER INFORMATION: May be any amino acid.
<221> NAME/KEY: UNSURE
<222> LOCATION: (239)
<223> OTHER INFORMATION: May be any amino acid.

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Val Ser Ile
            20                  25                  30

Ser Asn Tyr Leu Ala Trp Tyr Gln Gln Lys Pro Gly Lys Ala Pro Lys
        35                  40                  45

Leu Leu Ile Tyr Ala Ala Ser Ser Leu Glu Ser Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Asn Ser
                85                  90                  95
```

Leu Pro Glu Trp Thr Phe Gly Gln Gly Thr Lys Val Glu Ile Lys Gly
            100                 105                 110

Ser Thr Ser Gly Ser Gly Lys Pro Gly Ser Gly Glu Gly Ser Thr Lys
            115                 120                 125

Gly Glu Val Gln Leu Val Glu Ser Gly Gly Gly Leu Val Gln Pro Gly
        130                 135                 140

Gly Ser Leu Arg Leu Ser Cys Ala Ala Ser Gly Phe Thr Phe Ser Ser
145                 150                 155                 160

Tyr Ala Met Ser Trp Val Arg Gln Ala Pro Gly Lys Gly Leu Glu Trp
                165                 170                 175

Val Ser Val Ile Ser Gly Lys Thr Asp Gly Gly Ser Thr Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
        210                 215                 220

Tyr Tyr Cys Ala Arg Gly Arg Xaa Gly Xaa Ser Leu Ser Gly Xaa Tyr
225                 230                 235                 240

Tyr Tyr Tyr His Tyr Phe Asp Tyr Trp Gly Gln Gly Thr Leu Val Thr
                245                 250                 255

Val Ser Ser Lys Lys Lys Lys Lys Lys Lys Val Thr Val Ser Lys
            260                 265                 270

Lys Lys Lys Lys Lys Lys Val Thr Val Ser
            275                 280

<210> SEQ ID NO 7
<211> LENGTH: 282
<212> TYPE: PRT
<213> ORGANISM: Artificial Sequence
<220> FEATURE:
<223> OTHER INFORMATION: Description of Artificial Sequence: C6.5/218
      sFv

<400> SEQUENCE: 7

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly His Thr Asn Arg Pro Ala Gly Val Pro Asp Arg Phe Ser
    50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu Gly Gly
            100                 105                 110

Ser Thr Ser Gly Ser Gly Lys Pro Gly Ser Gly Glu Gly Ser Thr Lys
            115                 120                 125

Gly Gln Val Gln Leu Leu Gln Ser Gly Ala Glu Leu Lys Lys Pro Gly
        130                 135                 140

Glu Ser Leu Lys Ile Ser Cys Lys Gly Ser Gly Tyr Ser Phe Thr Ser
145                 150                 155                 160

Tyr Trp Ile Ala Trp Val Arg Gln Met Pro Gly Lys Gly Leu Glu Tyr

-continued

```
                165                 170                 175
Met Gly Leu Ile Tyr Pro Gly Asp Ser Asp Thr Lys Tyr Ser Pro Ser
            180                 185                 190

Phe Gln Gly Gln Val Thr Ile Ser Val Asp Lys Ser Val Ser Thr Ala
        195                 200                 205

Tyr Leu Gln Trp Ser Ser Leu Lys Pro Ser Asp Ser Ala Val Tyr Phe
    210                 215                 220

Cys Ala Arg His Asp Val Gly Tyr Cys Ser Ser Ser Asn Cys Ala Lys
225                 230                 235                 240

Trp Pro Glu Tyr Phe Gln His Trp Gly Gln Gly Thr Leu Val Thr Val
                245                 250                 255

Ser Ser Lys Lys Lys Lys Lys Lys Lys Val Thr Val Ser Lys Lys
                260                 265                 270

Lys Lys Lys Lys Lys Lys Val Thr Val Ser
            275                 280

<210> SEQ ID NO 8
<211> LENGTH: 84
<212> TYPE: PRT
<213> ORGANISM: Artificial Sequence
<220> FEATURE:
<223> OTHER INFORMATION: Description of Artificial Sequence: Nucleic
      acid binding region
<223> OTHER INFORMATION: Amino acids in positions 1-56 may be absent
      or present.
<221> NAME/KEY: UNSURE
<222> LOCATION: (57)..(76)
<223> OTHER INFORMATION: May be any amino acid.
<223> OTHER INFORMATION: Amino acids in positions 57-76 may be absent or
      present.

<400> SEQUENCE: 8

Lys Lys Lys Lys Lys Lys Lys Lys Lys Lys Lys Lys Lys Lys Lys Lys
  1               5                  10                  15

Lys Lys Lys Lys Lys Lys Lys Lys Lys Lys Lys Lys Lys Lys Lys Lys
             20                  25                  30

Lys Lys Lys Lys Lys Lys Lys Lys Lys Lys Lys Lys Lys Lys Lys Lys
         35                  40                  45

Lys Lys Lys Lys Lys Lys Lys Lys Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Lys Lys Lys Lys
 65                  70                  75                  80

Lys Lys Lys Lys

<210> SEQ ID NO 9
<211> LENGTH: 84
<212> TYPE: PRT
<213> ORGANISM: Artificial Sequence
<220> FEATURE:
<223> OTHER INFORMATION: Description of Artificial Sequence: Nucleic
      acid binding region
<223> OTHER INFORMATION: Amino acids in positions 1-56 may be absent or
      present.
<221> NAME/KEY: UNSURE
<222> LOCATION: (57)..(76)
<223> OTHER INFORMATION: May be any amino acid.
<223> OTHER INFORMATION: Amino acids in positions 57-76 may be absent or
      present.

<400> SEQUENCE: 9

Arg Arg Arg Arg Arg Arg Arg Arg Arg Arg Arg Arg Arg Arg Arg Arg
  1               5                  10                  15
```

-continued

```
Arg Arg Arg Arg Arg Arg Arg Arg Arg Arg Arg Arg Arg
        20                  25                  30

Arg Arg Arg Arg Arg Arg Arg Arg Arg Arg Arg Arg Arg
        35                  40                  45

Arg Arg Arg Arg Arg Arg Arg Arg Xaa Xaa Xaa Xaa Xaa Xaa Xaa
        50                  55                  60

Xaa Xaa Xaa Xaa Xaa Xaa Xaa Xaa Xaa Xaa Xaa Arg Arg Arg Arg
 65                  70                  75                  80

Arg Arg Arg Arg

<210> SEQ ID NO 10
<211> LENGTH: 83
<212> TYPE: PRT
<213> ORGANISM: Artificial Sequence
<220> FEATURE:
<223> OTHER INFORMATION: Description of Artificial Sequence: Nucleic
      acid binding region
<223> OTHER INFORMATION: Amino acids in positions 1-56 may be absent or
      present.
<221> NAME/KEY: UNSURE
<222> LOCATION: (57)..(76)
<223> OTHER INFORMATION: May be any amino acid.
<223> OTHER INFORMATION: Amino acids in positions 57-76 may be absent or
      present.

<400> SEQUENCE: 10

Arg Lys Arg Lys Arg Lys Arg Lys Arg Lys Arg Lys Arg Lys Arg Lys
 1               5                  10                  15

Arg Lys Arg Lys Arg Lys Arg Lys Arg Lys Arg Lys Arg Lys Arg Lys
        20                  25                  30

Arg Lys Arg Lys Arg Lys Arg Lys Arg Lys Arg Lys Arg Lys Arg Lys
        35                  40                  45

Arg Lys Arg Lys Arg Lys Arg Lys Xaa Xaa Xaa Xaa Xaa Xaa Xaa
        50                  55                  60

Xaa Xaa Xaa Xaa Xaa Xaa Xaa Xaa Xaa Xaa Xaa Arg Lys Arg Lys
 65                  70                  75                  80

Arg Lys Arg

<210> SEQ ID NO 11
<211> LENGTH: 84
<212> TYPE: PRT
<213> ORGANISM: Artificial Sequence
<220> FEATURE:
<223> OTHER INFORMATION: Description of Artificial Sequence: Nucleic
      acid binding region
<223> OTHER INFORMATION: Amino acids in positions 1-56 may be absent or
      present.
<221> NAME/KEY: UNSURE
<222> LOCATION: (57)..(76)
<223> OTHER INFORMATION: May be any amino acid.
<223> OTHER INFORMATION: Amino acids in positions 57-76 may be absent or
      present.

<400> SEQUENCE: 11

Arg Arg Arg Arg Arg Arg Arg Arg Arg Arg Arg Arg Arg Arg Arg
 1               5                  10                  15

Arg Arg Arg Arg Arg Arg Arg Arg Arg Arg Arg Arg Arg
        20                  25                  30

Arg Arg Arg Arg Arg Arg Arg Arg Arg Arg Arg Arg Arg
        35                  40                  45

Arg Arg Arg Arg Arg Arg Arg Arg Xaa Xaa Xaa Xaa Xaa Xaa Xaa
        50                  55                  60
```

-continued

```
Xaa Xaa Xaa Xaa Xaa Xaa Xaa Xaa Xaa Xaa Xaa Xaa Lys Lys Lys
65                  70                  75                  80

Lys Lys Lys Lys

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
gtcaccgtct ccaaaaagaa gaaaaaaaag aaaaag                                36

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
gtgacctttt tcttttttt cttcttttg aagacg                                  36
```

METHOD FOR TARGETED DELIVERY OF NUCLEIC ACIDS

The present application is a divisional application of U.S. Appl. Ser. No. 09/420,592, filed Oct. 19, 1999, now U.S. Pat. No. 6,333,396, which claims benefit of the filing date of U.S. Appl. No. 60/104,949, filed Oct. 20, 1998, each of which disclosure is incorporated herein in entirety by reference.

BACKGROUND OF THE INVENTION

1. Field of the Invention

The present invention is directed to a method of in vivo and ex vivo gene delivery, for a variety of cells. More specifically, it relates to a novel carrier system and method for targeted delivery of nucleic acids to mammalian cells. More specifically, the present invention relates to carrier systems comprising single-chain polypeptide binding molecules having a basic amino acid rich region, such as an oligo-lysine or an oligo-arginine region, and having the three dimensional folding and, thus, the binding ability and specificity, of the variable region of an antibody. Such preparations of modified single chain polypeptide binding molecules also have ability to bind nucleic acids at the basic amino acid rich region. These properties of the modified single chain polypeptide binding molecules make them very useful in a variety of therapeutic applications including gene therapy. The invention also relates to multivalent antigen-binding molecules having basic amino acid rich regions. Compositions of, genetic constructions for, methods of use, and methods for producing such basic amino acid rich region containing antigen-binding proteins are disclosed.

2. Background Art

Substantial attention has been given to the promise of gene therapy in recent years. This term has been used to describe a wide variety of methods using recombinant biotechnology techniques to deliver a variety of different materials to a cell. Such methods include, for example, the delivery of a gene, antisense RNA, a cytotoxic agent, etc., by a vector to a mammalian cell, preferably a human cell either in vivo or ex vivo. Most of the initial work has focused on the use of retroviral vectors to transform these cells. This focus has resulted from the ability of retroviruses to infect cells with high efficiency.

However, numerous difficulties with retroviruses have been reported. For example, problems have been encountered in infecting certain cell types. Retroviruses typically enter cells via receptors and if such receptors are not present on the cell, or not present in large numbers, then infection is not possible or efficient. These viruses are also relatively labile in comparison to other viruses. Outbreaks of wild-type virus from recombinant virus-producing cell lines have also been reported with the vectors themselves causing disease. Moreover, these viruses are only expressed in dividing cells.

In addition, retroviral-mediated gene transfer methods typically result in stable transformation of the target cells. Although this may be regarded as advantageous, the stable transformation of a patient's somatic cells makes it difficult to reverse the treatment regimen if undesirable side effects occur. Moreover, there is the concern that genetic transformation might lead to malignant transformation of the cell.

Other methods of delivering genetic material to cells in vivo and ex vivo include the use of liposome entrapped DNA. Liposomes are small membrane-enclosed spheres that have been formed with the appropriate DNA entrapped within it. However, this system also has inherent problems. It is difficult to control the size of the liposome and, hence the uniformity of delivery to individual cells. Additionally, it is difficult to prevent leakage of the contents of the liposomes and as with other techniques, there has been difficulty in directing cell-type specificity.

Antibodies are proteins generated by the immune system to provide a specific molecule capable of complexing with an invading molecule, termed an antigen. Natural antibodies have two identical antigen-binding sites, both of which are specific to a particular antigen. The antibody molecule "recognizes" the antigen by complexing its antigen-binding sites with areas of the antigen termed epitopes. The epitopes fit into the conformational architecture of the antigen-binding sites of the antibody, enabling the antibody to bind to the antigen.

The antibody molecule is composed of two identical heavy and two identical light polypeptide chains, held together by interchain disulfide bonds. The remainder of this discussion on antibodies will refer only to one pair of light/heavy chains, as each light/heavy pair is identical. Each individual light and heavy chain folds into regions of approximately 110 amino acids, assuming a conserved three-dimensional conformation. The light chain comprises one variable region ($V_L$) and one constant region ($C_L$), while the heavy chain comprises one variable region ($V_H$) and three constant regions ($C_H1$, $C_H2$ and $C_H3$). Pairs of regions associate to form discrete structures. In particular, the light and heavy chain variable regions associate to form an "Fv" area which contains the antigen-binding site. The constant regions are not necessary for antigen binding and in some cases can be separated from the antibody molecule by proteolysis, yielding biologically active (i.e., binding) variable regions composed of half of a light chain and one quarter of a heavy chain.

Further, all antibodies of a certain class and their $F_{ab}$ fragments (i.e., fragments composed of $V_L$, $C_L$, $V_H$, and $C_H1$) whose structures have been determined by x-ray crystallography show similar variable region structures despite large differences in the sequence of hypervariable segments even when from different animal species. The immunoglobulin variable region seems to be tolerant towards mutations in the antigen-binding loops. Therefore, other than in the hypervariable regions, most of the so-called "variable" regions of antibodies, which are defined by both heavy and light chains, are, in fact, quite constant in their three dimensional arrangement. See for example, Huber, R., Science 233:702–703 (1986).

Recent advances in immunobiology, recombinant DNA technology, and computer science have allowed the creation of single polypeptide chain molecules that bind antigen. These single-chain antigen-binding molecules ("SCA") or single-chain variable fragments of antibodies ("sFv") incorporate a linker polypeptide to bridge the individual variable regions, $V_L$ and $V_H$, into a single polypeptide chain. A description of the theory and production of single-chain antigen-binding proteins is found in Ladner et al., U.S. Pat. Nos. 4,946,778, 5,260,203, 5,455,030 and 5,518,889. The single-chain antigen-binding proteins produced under the process recited in the above U.S. patents have binding specificity and affinity substantially similar to that of the corresponding Fab fragment. A computer-assisted method for linker design is described more particularly in Ladner et al., U.S. Pat. Nos. 4,704,692 and 4,881,175, and WO 94/12520.

The in vivo properties of sFv polypeptides are different from MAbs and antibody fragments. Due to their small size, sFv polypeptides clear more rapidly from the blood and penetrate more rapidly into tissues (Milenic, D. E. et al., Cancer Research 51:6363–6371 (1991); Colcher et al., *J Natl. Cancer Inst.* 82:1191 (1990); Yokota et al., *Cancer Research* 52:3402 (1992)). Due to lack of constant regions, sFv polypeptides are not retained in tissues such as the liver and kidneys. Due to the rapid clearance and lack of constant regions, sFv polypeptides will have low immunogenicity. Thus, sFv polypeptides have applications in cancer diagnosis and therapy, where rapid tissue penetration and clearance, and ease of microbial production are advantageous.

A multivalent antigen-binding protein has more than one antigen-binding site. A multivalent antigen-binding protein comprises two or more single-chain protein molecules. Enhanced binding activity, di- and multi-specific binding, and other novel uses of multivalent antigen-binding proteins have been demonstrated. See, Whitlow, M., et al., *Protein Engng.* 7:1017–1026 (1994); Hoogenboom, H.R., *Nature Biotech.* 15:125–126 (1997); and WO 93/11161.

Ladner et al. also discloses the use of the single chain antigen binding molecules in diagnostics, therapeutics, in vivo and in vitro imaging, purifications, and biosensors. The use of the single chain antigen binding molecules in immobilized form, or in detectably labeled forms is also disclosed, as well as conjugates of the single chain antigen binding molecules with therapeutic agents, such as drugs or specific toxins, for delivery to a specific site in an animal, such as a human patient.

Whitlow et al. (*Methods.: A Companion to Methods in Enzymology* 2(2):97–105 (June, 1991)) provide a good review of the art of single chain antigen binding molecules and describe a process for making them.

In U.S. Pat. 5,091,513, Huston et al. discloses a family of synthetic proteins having affinity for preselected antigens. The contents of U.S. Pat. 5,091,513 are incorporated by reference herein. The proteins are characterized by one or more sequences of amino acids constituting a region that behaves as a biosynthetic antibody binding site (BABS). The sites comprise (1) noncovalently associated or disulfide bonded synthetic $V_H$ and $V_L$ regions, (2) $V_H$—$V_L$ or $V_L$—$V_H$ single chains wherein the $V_H$ and $V_L$ are attached to a polypeptide linker, or (3) individual $V_H$ or $V_L$ domains. The binding domains comprises complementarity determining regions (CDRs) linked to framework regions (FRs), which can be derived from separate immunoglobulins.

U.S. Pat. 5,091,513 also discloses that three subregions (the CDRs) of the variable domain of each of the heavy and light chains of native immunoglobulin molecules collectively are responsible for antigen recognition and binding. These CDRs consist of one of the hypervariable regions or loops and of selected amino acids or amino acid sequences disposed in the framework regions that flank that particular hypervariable region. It is said that framework regions from diverse species are effective in maintaining CDRs from diverse other species in proper conformation so as to achieve true immunochemical binding properties in a biosynthetic protein.

U.S. Pat. No. 5,091,513 includes a description of a chimeric polypeptide that is a single chain composite polypeptide comprising a complete antibody binding site. This single chain composite polypeptide is described as having a structure patterned after tandem $V_H$ and $V_L$ domains, with a carboxyl terminal of one attached through an amino acid sequence to the amino terminal of the other. It thus comprises an amino acid sequence that is homologous to a portion of the variable region of an immunoglobulin heavy chain ($V_H$) peptide bonded to a second amino acid sequence that was homologous to a portion of the variable region of an immunoglobulin light chain ($V_L$)

Chen et al., describe the production and use of a fusion protein consisting of an antibody Fab fragment and a DNA binding moiety, protamine, to deliver toxin-expressing plasmid DNA into HIV infected cells by receptor mediated endocytosis (S-Y Chen et al., *Gene Therapy* 2: 116–123 (1995)).

BRIEF SUMMARY OF THE INVENTION

Accordingly, it is an object of the present invention to provide a new and improved delivery system that can introduce foreign genes in a non-toxic, cell specific manner into mammalian cells. Also provided by the invention is a system and an efficient method that exhibits a high degree of cell specificity using relatively simple yet reliable delivery.

Another feature of the present invention is the use of receptor-mediated specificity to provide cell specificity to the gene delivery system. This involves the use of cell-surface receptors as naturally existing entry mechanisms for the specific delivery of genes. The molecules once recognized and bound to the receptor can be internalized within the target cell via endocytosis. Included in this feature is the provision for a unique carrier comprising a single-chain antigen-binding protein/polynucleotide complex capable of targeting the gene to specific cells possessing particular receptors that recognize the complex.

In addition, the carrier of the present invention relates to tailed single chain polypeptides containing a basic amino acid rich region (i.e., oligo-lysine, oligo-arginine, or a mixture thereof) and having binding affinity for an antigen and the capability of delivering nucleic acids to a cell and processes for preparing them. Suitable polypeptides are, for example, those described by Ladner et al. in U.S. Pat. No. 4,946,778 and Huston et al. in U.S. Pat. No. 5,091,513.

These features provide advantages to the present invention that directly contribute to the efficiency and target specificity of the delivery system to specific cell types, including normal cells as well as tumor cells not found in the delivery systems known in the art.

The present invention is directed to a method of delivering nucleic acids to a cell comprising:

(1) providing an a basic amino acid tailed single-chain antigen-binding polypeptide capable of delivering nucleic acids to a cell comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein, at its C-terminus, N-terminus, or both of polypeptide (a), (b) or both, the single-chain antigen-binding polypeptide has an amount of basic amino acid residues sufficient to bind nucleic acids, wherein the basic amino acid residues are selected from the group consisting of: Lys, Arg and a combination thereof; and wherein the basic amino acid residues binds nucleic acid and wherein the single-chain antigen-binding polypeptide binds antigen;

(2) allowing a nucleic acid to bind to the basic amino acid residue containing single-chain antigen-binding polypeptide; and (3) transforming a cell with the nucleic acid bound basic amino acid residue containing single-chain antigen-binding polypeptide.

More particularly, the invention is directed to a single-chain antigen-binding polypeptide capable of delivering nucleic acids to a cell, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein at its C-terminus, N-terminus, or both of polypeptide (a), (b) or both, the single-chain antigen-binding polypeptide has an amount of basic amino acid residues sufficient to bind nucleic acids, wherein the basic amino acid residues are selected from the group consisting of: Lys, Arg and a combination thereof; and wherein the basic amino acid residues binds nucleic acid and wherein the single-chain antigen-binding polypeptide binds antigen. These basic amino acid residues in the sFv protein (e.g., oligo-lysine sFv) generate a minimal non-specific nucleic acid binding region. The basic amino acid region is configured such that at least 2 to 8 groups of eight consecutive residues of Lys, Arg or a combination thereof are separated from adjacent groups by 0–20 amino acid residues.

The invention is further directed to a genetic sequence encoding a single-chain antigen-binding polypeptide capable of delivering nucleic acids to a cell, comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein at its C-terminus, N-terminus, or both of polypeptide (a), (b) or both, the single-chain antigen-binding polypeptide has an amount of basic amino acid residues sufficient to bind nucleic acids, wherein the basic amino acid residues are selected from the group consisting of: Lys, Arg and a combination thereof, and wherein the basic amino acid residues binds nucleic acid and wherein the single-chain antigen-binding polypeptide binds antigen. These basic amino acid residues in the sFv protein (e.g., oligo-lysine sFv) generate a minimal non-specific nucleic acid binding region. The basic amino acid region is configured such that at least 2 to 8 groups of eight consecutive residues of Lys, Arg or a combination thereof are separated from adjacent groups by 0–20 amino acid residues.

The nucleic acid is a polynucleotide that can be either DNA or RNA.

The invention is directed to a replicable cloning or expression vehicle comprising the above described polynucleotide sequence. The invention is also directed to such vehicle which is a plasmid. The invention is further directed to a host cell transformed with the above described DNA. The host cell can be a bacterial cell, a yeast cell or other fungal cell, an insect cell or a mammalian cell line. A preferred host is *Pichia pastoris.*

The invention is directed to a method of producing a single-chain antigen-binding polypeptide capable of delivering nucleic acids to a cell, comprising:

(a) providing a first genetic sequence encoding a first polypeptide comprising the antigen binding portion of the variable region of an antibody heavy or light chain;

(b) providing a second genetic sequence encoding a second polypeptide comprising the antigen binding portion of the variable region of an antibody heavy or light chain; and (c) linking the first and second genetic sequences (a) and (b) with a third genetic sequence encoding a peptide linker into a fourth genetic sequence encoding a single chain polypeptide having an antigen binding site, wherein at its C-terminus, N-terminus, or both of polypeptide (a), (b) or both, the single-chain antigen-binding polypeptide has an amount of basic amino acid residues sufficient to bind nucleic acids, wherein the basic amino acid residues are selected from the group consisting of: Lys, Arg and a combination thereof; and wherein the basic amino acid residues binds nucleic acid and wherein the single-chain antigen-binding polypeptide binds antigen;

(d) transforming a host cell with the fourth genetic sequence encoding a single-chain antigen-binding polypeptide of (c); and (e) expressing the single-chain antigen-binding polypeptide of (c) in the host, thereby producing a single-chain antigen-binding polypeptide capable of delivering nucleic acids to a cell.

The invention is further directed to a multivalent single-chain antigen-binding protein, comprising two or more single-chain antigen-binding polypeptides, each single-chain antigen-binding polypeptide comprising:

(a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein at its C-terminus, N-terminus, or both of polypeptide (a), (b) or both, the single-chain antigen-binding polypeptide has an amount of basic amino acid residues sufficient to bind nucleic acids, wherein the basic amino acid residues are selected from the group consisting of. Lys, Arg and a combination thereof; and wherein the basic amino acid residues binds nucleic acid and wherein the single-chain antigen-binding polypeptide binds antigen.

In the above described embodiments of the invention, a lysine rich or an oligo-Lys polypeptide sequence of the present invention can be capable of attaching a polyalkylene oxide moiety wherein the polyalkylene oxide conjugated oligo-lysine tailed single-chain antigen-binding polypeptide binds an antigen as well as nucleic acids.

In the above described embodiments of the invention, the C-terminus of the second polypeptide (b) can be the native C-terminus. The C-terminus of the second polypeptide (b) can comprise a deletion of one or plurality of amino acid residue(s), such that the remaining N-terminus amino acid residues of the second polypeptide are sufficient for the polypeptide to be capable of binding an antigen. The C-terminus of the second polypeptide can comprise an addition of one or plurality of amino acid residue(s), such that the polypeptide is capable of binding an antigen. Moreover, the nucleic acid binding region can be generated by mutating one or a plurality of amino acid residue(s) to a basic amino acid residue(s) in the C-terminal or N-terminal regions of the polypeptide (a) or (b). In addition, the nucleic acid binding region can be generated by inserting blocks of basic amino acids at the C-terminus or N-terminus of the polypeptide (a) or (b).

In a preferred embodiment of the invention, the first polypeptide (a) can comprise the antigen binding portion of the variable region of an antibody light chain and the second polypeptide (b) comprises the antigen binding portion of the variable region of an antibody heavy chain.

The invention is also directed to a method for treating a targeted disease, comprising administering an effective amount of a composition comprising a nucleic acid molecule bound to the polypeptide or protein of the invention and a pharmaceutically acceptable carrier vehicle for delivery to a cell.

BRIEF DESCRIPTION OF THE DRAWINGS/ FIGURES

FIG. 1 shows the DNA (SEQ ID NO: 1) and protein sequence (SEQ ID NO: 2) of CC49/218 sFv with an engineered oligo-lysine C-terminal tail segment. The eight new lysine residues were genetically engineered at a BstEII site and are shown underlined and marked with asterisks. Also highlighted are the CDR sequences (double underlined), the 218 linker (underlined and labeled) and selected restriction sites.

FIGS. 2A and 2B show the DNA (SEQ ID NO: 3) and protein sequence (SEQ ID NO: 4) of CC49/218 sFv with an engineered oligo-lysine C-terminal tail segment. The sixteen new lysine residues were genetically engineered at a BstEII site and are shown underlined and marked with asterisks. Also highlighted are the CDR sequences (double underlined), the 218 linker (underlined and labeled) and selected restriction sites.

FIG. 3 shows the protein sequence (SEQ ID NO: 5) of A33/218 sFv with engineered oligo-lysine C-terminal tail segment. The sixteen new lysine residues are marked with asterisks. Also highlighted are the CDR sequences (double underline) and the 218 linker (overlined and labeled).

FIG. 4 shows DNA binding by A33/218 SCA with an engineered 16 lysine C-terminal tail using gel shift assay: lane 1 is a BSA control, lane 2 is a GS115 culture supernatant control and lanes 3–12 have 0, 5, 10, 15, 20, 30, 40, 50, 60, 70 and 80 µl, respectively of dialyzed culture supernatant of the 16 lysine SCA protein.

FIG. 5 shows the Coomassie Blue stained SDS-PAGE gel of purified CC49-16K 266(7). Lane 1, molecular weight markers; Lane 2, purified native CC49/218 sFv; Lane 3, EN266(7) fermentation cell pellet; Lane 4, EN266(7) sFv released from Lane 3 material by a high salt wash (1.5 M NaCl, 20 mM Tris-HCl, pH 8.0, at room temperature for 2 hours).

Figure 4:

FIG. 8 shows the sequence for Kabat Consensus $V_K I/218/V_H III$ sFv (SEQ ID NO: 6). The sixteen new lysine residues are marked with asterisks. CDR sequences are double underlined.

FIG. 9 shows the sequence for C6.5/218 sFv (SEQ ID NO: 7). The sixteen new lysine residues are marked with asterisks. CDR sequences are double underlined.

DETAILED DESCRIPTION OF THE INVENTION

The present invention is directed to the novel combination of a single-chain polypeptide containing basic amino acid region (e.g., regions rich in basic amino acids, oligo-lysine, oligo-arginine or combination thereof) and having 1) capability to bind nucleic acids; and 2) binding affinity for an antigen, such that the polypeptide is capable of delivering nucleic acids to cells. The present invention is also directed to a method of delivering nucleic acids to cells using a basic amino acid tailed single chain polypeptide. Furthermore, the foregoing design could applied not only to sFvs but also to $V_H$ single domains, disulfied-stabilized Fv, Fabs or Mabs.

Gene Delivery Methods

The present invention provides a novel delivery system that can introduce foreign genes in a non-toxic, cell specific manner into mammalian cells ex vivo or in vivo. Also provided by the invention is a system and method that exhibits a high degree of cell specificity using relatively simple yet reliable delivery.

The present invention uses a receptor-mediated specificity to provide cell specificity to the gene delivery system. This involves the use of cell-surface receptors or antigens as naturally existing entry mechanisms for the specific delivery of genes. Included in this feature is the provision for a unique basic amino acid tailed single-chain antigen-binding polypeptide polynucleotide complex capable of targeting the gene to specific cells possessing particular receptors or antigens that are recognized by the complex. Cell specificity can be achieved by selecting a single-chain antigen-binding protein that has a binding affinity for the cell type to be targeted for gene delivery. For example, anti-tumor single-chain antigen-binding protein can be used to target gene delivery to specific tumor cells. Also, anti-fluorescein single-chain antigen-binding proteins can be used to target fluorescein labeled cells. Thus, the skilled artisan could readily target any cell type by selecting a single-chain antigen-binding protein having an appropriate affinity for the targeted cell.

In addition, the cell specificity for the targeted delivery of nucleic acids can be achieved or enhanced by including "translocation domains" in the sFvs of the present invention. The use of the exotoxin A "translocation domain" has been demonstrated to facilitate efficient DNA transfer in non-viral DNA delivery systems. See, Fominaya et al. *J Biol. Chem.* 271: 10560 (1986); and WO 96/13599, incorporated by reference). Also, nucleus targeting peptide fusions have demonstrated enhanced delivery of DNA to the nucleus in non-viral DNA delivery systems. (See, Avrameas et al. *Proc. Natl. Acad. Sci.* 95: 5601–5606 (1998)). Thus, the skilled artisan could readily further enhance the efficiency nucleic acid delivery to a target cell type by including "translocation domain" and or a nucleus targeting peptide within a single-chain antigen-binding protein which has an appropriate affinity for the targeted cell.

The present invention is directed to a method of delivering nucleic acids to a cell comprising:
(1) providing an basic amino acid tailed single-chain antigen-binding polypeptide capable of delivering nucleic acids to a cell comprising:
    (a) a first polypeptide comprising the antigen binding portion of the variable region of an antibody heavy or light chain;

(b) a second polypeptide comprising the antigen binding portion of the variable region of an antibody heavy or light chain; and (c) a peptide linker linking the first and second polypeptides (a) and (b) into a single chain polypeptide having an antigen binding site, wherein at its C-terminus, N-terminus, or both of polypeptide (a), (b) or both, the single-chain antigen-binding polypeptide has an amount of basic amino acid residues sufficient to bind nucleic acids, wherein the basic amino acid residues are selected from the group consisting of: Lys, Arg and a combination thereof; and wherein the basic amino acid residues binds nucleic acid and wherein the single-chain antigen-binding polypeptide binds antigen;

(2) allowing a nucleic acid to bind to the basic amino acid tailed single-chain antigen-binding polypeptide; and (3) transforming a cell with the nucleic acid bound basic amino acid tailed single-chain antigen-binding polypeptide.

The invention also provides for the use of the basic amino acid tailed sFv proteins (i.e., oligo-Lys, oligo-Arg or oligo combination of lys and arg residues; or regions rich in lys and/or arg residues) in a process for targeted gene therapy. The invention further provides for sFv proteins having an amount of basic amino acid residues sufficient to bind nucleic acids. More specifically, the invention provides for sFv proteins having at least 10, 12, 14 or 16 lysines in the C-terminal region of the sFv which bind nucleic acids wherein the lysine residues are configured in two groups of eight consecutive lysine residues separated by 0–20 amino acid residues. A 16 lysine C-terminal tailed SCA protein complexed to a nucleic acid construct capable of expressing a protein, can be used to deliver such nucleic acid constructs to a specific cell type for (1) transient expression of the protein or (2) allow for the DNA construct to be inserted safely into the genome and have the expression be regulated by normal cellular signals. To target the nucleic acid delivery to a specific cell type, an SCA protein is selected that will bind to and be internalized by that cell type. Many such SCA proteins are well known to those skilled in the art. For example, anti-tumor SCAs can be modified to have a 16 lysine C-terminal tail according to the present invention. These anti-tumor SCAs can be used to carry DNA encoding toxins or chemotherapeutic proteins that, when internalized and expressed, will cause the death of the tumor cell.

Furthermore, PEGylating the oligo-lysine containing SCA protein or according to the methods disclosed in U.S. application Ser. No. 09/069,842, filed on Apr. 30, 1998 (incorporated by reference in its entirety), will also provide protection from degradation for the complexed nucleic acid since the modified SCA proteins have reduced immunogenicity and antigenicity as well a longer half-life in the bloodstream. In addition, an SCA protein having one or more lysine residues in a basic amino acid rich region will allow for site specific PEGylation at the lysine residue(s).

As indicated above, the single-chain antigen-binding polypeptides have a nucleic acid binding region comprising a sufficient amount of basic amino acids to bind nucleic acids. This region can comprise a sequence that is rich in basic amino acids such as lysine, arginine and combinations thereof. This region will contain enough basic amino acids to obtain the requisite overall positive charge on the sFv for nucleic acid binding. These nucleic acid binding regions can be at the C-terminal region, N-terminal region or both of the sFv. The nucleic acid binding regions can be generated by mutating one or a plurality of amino acid residue(s) of the sFv or by adding a block of basic amino acid residues to the C-terminal region, N-terminal region or both of the sFv. Furthermore, the foregoing design could be applied not only to sFvs but also to $V_H$ single domains, disulfide-stabilized Fv, Fabs or Mabs.

Preferably, the single-chain antigen-binding polypeptide according to the present invention has an amount of oligo-Lys, oligo-Arg or oligo-Lys/Arg residues sufficient to bind nucleic acids. Preferably, the nucleic acid binding region of single-chain antigen-binding polypeptide comprises at least 2 to 8 groups of eight consecutive Lys residues, Arg residues or a combination thereof, wherein each group of eight consecutive lysine, arg or lys/arg residues is separated from adjacent groups by 0–20 amino acid residues. More preferably, the nucleic acid binding region of the single-chain antigen-binding polypeptide comprises at least 2 to 6 groups of eight consecutive Lys residues, Arg residues or a combination thereof, wherein each group of eight consecutive lysine, arg or lys/arg residues is separated from adjacent groups by 0–20 amino acid residues. Still more preferably, the nucleic acid binding region of the single-chain antigen-binding polypeptide comprises at least 2 to 4 groups of eight consecutive Lys residues, Arg residues or a combination thereof, wherein each group of eight consecutive lysine, arg or lys/arg residues is separated from adjacent groups by 0–20 amino acid residues. More preferably, the nucleic acid binding region of the single-chain antigen-binding polypeptide comprises at least 2 to 3 groups of eight consecutive Lys residues, Arg residues or a combination thereof, wherein each group of eight consecutive lysine, arg or lys/arg residues is separated from adjacent groups by 0–20 amino acid residues. Still more preferably, the nucleic acid binding region of the single-chain antigen-binding polypeptide has at least 2 groups of eight consecutive Lys residues, Arg residues or a combination thereof, wherein each group of eight consecutive lysine, arg or lys/arg residues is separated from adjacent groups by 0–20 amino acid residues.

The nucleic acid binding regions of the single-chain antigen-binding polypeptide of the present invention can be represented by the following formulas: 1) (KKKKKKKK)m (X)n (KKKKKKKK) (SEQ ID NO: 8), wherein K is lysine, m is an integer between 1 and 7 and n is an integer between 0 and 20; 2) (RRRRRRRR)m (X)n (RRRRRRRR) (SEQ ID NO: 9), wherein R is Arginine, m is an integer between 1 and 7 and n is an integer between 0 and 20; 3) (RKRKRKRK)m (X)n (RKRKRKRK) (SEQ ID NO: 10), wherein K is lysine R is arginine such that the K and R residues either alternate or are in random order, m is an integer between 1 and 7 and n is an integer between 0 and 20; and 4) (RRRRRRRR)m (X)n (KKKKKKKK) (SEQ ID NO: 11), wherein K is lysine, R is arginine, m is an integer between 1 and 7 and n is an integer between 0 and 20. Preferably, the nucleic acid binding regions of the single-chain antigen-binding polypeptide of the present invention can be represented by the following formulas:1) (KKKKKKKK)m (X)n (KKKKKKKK) (SEQ ID NO: 8), wherein K is lysine, m is an integer between 1 and 5 and n is an integer between 0 and 20; 2) (RRRRRRRR)m (X)n (RRRRRRRR) (SEQ ID NO: 9), wherein R is Arginine, m is an integer between 1 and 5 and n is an integer between 0 and 20; 3) (RKRKRKRK)m (X)n (RKRKRKRK) (SEQ ID NO: 10), wherein K is lysine R is arginine such that the K and R residues either alternate or are in random order, m is an integer between 1 and 5 and n is an integer between 0 and 20; and 4) (RRRRRRRR)m (X)n (KKKKKKKK) (SEQ ID NO: 11), wherein K is lysine, R is arginine, m is an integer between 1 and 5 and n is an integer between 0 and 20.

More preferably, the nucleic acid binding regions of the single-chain antigen-binding polypeptide of the present invention can be represented by the following formulas: 1) (KKKKKKKK)m (X)n (KKKKKKKK) (SEQ ID NO: 8), wherein K is lysine, m is an integer between 1 and 3 and n is an integer between 0 and 20; 2) (RRRRRRRR)m (X)n (RRRRRRRR) (SEQ ID NO: 9), wherein R is Arginine, m is an integer between 1 and 3 and n is an integer between 0 and 20; 3) (RKRKRKRK)m (X)n (RKRKRKRK) (SEQ ID NO: 10), wherein K is lysine R is arginine such that the K and R residues either alternate or are in random order, m is an integer between 1 and 3 and n is an integer between 0 and 20; and 4) (RRRRRRRR)m (X)n (KKKKKKKK) (SEQ ID NO: 11), wherein K is lysine, R is arginine, m is an integer between 1 and 3 and n is an integer between 0 and 20.

Still more preferably, the nucleic acid binding regions of the single-chain antigen-binding polypeptide of the present invention can be represented by the following formulas: 1) (KKKKKKKK)m (X)n (KKKKKKKK) (SEQ ID NO: 8), wherein K is lysine, m is an integer between 1 and 2 and n is an integer between 0 and 20; 2) (RKRRKRRR)m (X)n (RRRRRRRR) (SEQ ID NO: 9), wherein R is Arginine, m is an integer between 1 and 2 and n is an integer between 0 and 20; 3) (RKRKRKRK)m (X)n (RKRKRKRK) (SEQ ID NO: 10), wherein K is lysine R is arginine such that the K and R residues either alternate or are in random order, m is an integer between 1 and 2 and n is an integer between 0 and 20; and 4) (RRRRRRRR)m (X)n (KKKKKKKK) (SEQ ID NO: 11), wherein K is lysine, R is arginine, m is an integer between 1 and 2 and n is an integer between 0 and 20. More preferably, the DNA binding regions of the single-chain antigen-binding polypeptide of the present invention can be represented by the following formulas: 1) (KKKKKKKK)m (X)n (KKKKKKKK) (SEQ ID NO: 8), wherein K is lysine, in is 1 and n is an integer between 0 and 20; 2) (RRRRRRRR)m (X)n (RRRRRRRR) (SEQ ID NO: 9), wherein R is Arginine, m is 1 and n is an integer between 0 and 20; 3) (RKRKRKRK)m (X)n (RKRKRKRK) (SEQ ID NO: 10), wherein K is lysine R is arginine such that the K and R residues either alternate or are in random order, m is 1 and n is an integer between 0 and 20; and 4) (RRRRRRRR)m (X)n (KKKKKKKK) (SEQ ID NO: 11), wherein K is lysine, R is arginine, m is 1 and n is an integer between 0 and 20.

Even more preferably, the single-chain antigen-binding polypeptide has the basic amino acid residue rich region, oligo-lysine residues, oligo-arginine residues or combination thereof, configured such that the number of groups of Lys and or Arg residues is no higher than that which would result in an unstable polynucleotide encoding the single-chain antigen-binding polypeptide or significantly reduce the efficiency of translation of the polynucleotide encoding the single-chain antigen-binding polypeptide or interfere with antigen binding.

The preferred ratio of single-chain antigen-binding polypeptide to nucleic acid are as follows: 10,000:1, 2000:1, 1000:1, 500:1, 250:1 or 100:1 (molar ratio of sFv: DNA). Of course, these ranges are exemplary only and one of skill in the art could readily optimize the ratios for optimal binding and transfection results for any particular cell or tissue type.

The optimal conditions for complexing the nucleic acids with the sFv of the present invention is as follows. Preferably, the complexing is performed in a complexing buffer containing 0–100 mM Tris-HCl (or any equivalent buffer), 5–500 mM NaCl, pH 6–9. More preferably, the complexing is performed in a buffer containing 10 mM Tris-HCl, 150 mM NaCl, pH 7.5. The time and temperature for complexing the nucleic acids with the sFv in the foregoing complexing buffer are 1 to 120 minutes at 4–40° C. The preferred time and temperature for complexing the nucleic acids with the sFv in the complexing buffer are 15 minutes at room temperature or about 22° C.

Chen et al. described the production and use of a fusion protein consisting of an antibody Fab fragment and a DNA binding moiety, protamine, to deliver toxin-expressing plasmid DNA into HIV infected cells by receptor mediated endocytotsis. S-Y Chen et al., (1995) *Gene Therapy* 2:116–123. The present invention, however, has advantages over the Fab-protamine fusion peptide for delivering DNA into cells as disclosed by Chen et al. This is because, protamine or poly lysine domains (of a 100 lysine residues or more, i.e., "100K") are very tight binders of DNA compared to the "16K" tail of the present invention. The present inventors, however, have discovered that the oligo lysine configuration of the present invention having 16 lysines ("16K") placed within a short C-terminal extension from the sFv behaves as a minimal nucleic acid-binding domain. (See, for example, FIGS. 2A, 2B and 3 and Examples 1 and 3). This is because the natural DNA binding protein like protamine interacts with DNA presumably by electrostatic interactions, hydrogen bonding, hydrophobic bonds, Van der Waals bonds, and overall shape complementarity. However, in contrast to most natural DNA binding proteins, the sFv containing a basic amino acid rich region according to the present invention is proposed to bind and complex with nucleic acids essentially through electrostatic interactions and interpolyelectrolyte complex chemistry.

Moreover, Pardridge et al (*J. Pharma. and Experimetal Therapeutics* 286:548–554 (1998)) have shown that "cationization" promotes endocytosis of Mabs. Thus, the sFv having a basic amino acid rich region according to the present invention can be more readily taken up by endocytosis due an increased positive charge of the sFv. An increase in endocytosis is expected to result in increased transfection efficiencies and expression of the nucleic acids that are complexed with the sFv of the present invention.

The use of sFv fused to a minimal nucleic acid-binding domain can also have production advantages. Although, proteins such as protamine or polylysine having 100 or more lysines can be more effective at condensing DNA, the expected reduction in affinity of the 16K tail for DNA, relative to protamine, will have the advantage of releasing the nucleic acid more efficiently from the sFv once targeting has been achieved, thereby allowing this nucleic acid to be expressed by the cell. Thus, the 16K tailed sFv of the present can be a more effective nucleic acid delivery vehicle than the Fab-protamine or Fab-polylysine (100K) synthetic polypeptides disclosed in the art. The oligo-lysine or oligo-arginine tail strategy of the present invention can be amenable to PEGylation as discussed, supra, which results in a DNA delivery carrier with reduced immunogenicity and increased half-life.

As shown in Examples 5 and 6, below, the 16K sFv of the present invention can be employed as a targeting molecule to enhance transfection of specific cells in culture. The demonstration of DNA delivery to cultured cells by in situ immunochemistry shows that the SCA molecule of the present invention can accomplish specific targeting, even for targets that are non-internalizing. In addition, transfection was also shown to be markedly enhanced by the oligo-lysine sFv of the present invention. Since the oligo-lysine sFv of the present invention has demonstrated to be successful in transfecting targets that are non internalizing, it is anticipated that the enhanced specific transfection of an internalizing target should also be achievable.

The nucleic acid used in the present invention can have a therapeutic effect on the target cell, the effect selected from, but not limited to, correcting a defective gene or protein, a drug action, a toxic effect, a growth stimulating effect, a growth inhibiting effect, a metabolic effect, a catabolic affect, an anabolic effect, an antiviral effect, an antibacterial effect, a hormonal effect, a neurohumoral effect, a cell differentiation stimulatory effect, a cell differentiation inhibitory effect, a neuromodulatory effect, an antineoplastic effect, an anti-tumor effect, an insulin stimulating or inhibiting effect, a bone marrow stimulating effect, a pluripotent stem cell stimulating effect, an immune system stimulating effect, and any other known therapeutic effects that can be provided by a therapeutic agent delivered to a cell via a delivery system according to the present invention.

The sFv conjugate of the present invention can be used for protection, suppression or treatment of infection or disease. By the term "protection" from infection or disease as used herein is intended "prevention," "suppression" or "treatment." "Prevention" involves administration of a sFv conjugate prior to the induction of the disease. "Suppression" involves administration of the composition prior to the clinical appearance of the disease.

"Treatment" involves administration of the protective composition after the appearance of the disease. It will be understood that in human and veterinary medicine, it is not always possible to distinguish between "preventing" and "suppressing" since the ultimate inductive event or events can be unknown, latent, or the patient is not determined until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

Further, essentially all of the uses for which monoclonal or polyclonal antibodies, or fragments thereof, have been envisioned by the prior art, can be addressed by the oligolysine tailed sFv proteins of the present invention. See, e.g., Kohler et al., *Nature* 256:495 (1975); Kohler et al, *Eur. J Immunol.* 6:511 (1976); Kohler et al., *Eur. J. Immunol.* 6:292 (1976); Hammerling et al., in: *Monoclonal Antibodies and T-Cell Hybridomas*, pp.563–681, Elsevier, N (1981); Sambrook et al., *Molecular Cloning—A Laboratory Manual*, 2 nd ed., Cold Spring Harbor Laboratory (1989).

The gene delivery system of the present invention can be used for any host. Preferably, the host will be a mammal. Preferred mammals include primates such as humans and chimpanzees, domestic animals such as horses, cows, pigs, dogs, and cats. More preferably, the host animal is a primate or domestic animal. Still more preferably, the host animal is a primate such as a human.

Because humans are the desired hosts for in vivo delivery, certain test models have been developed and accepted by the field to determine the efficacy and utility of a delivery system. This involves in vitro testing, ex vivo testing and use of marker genes. Thus, the susceptibility of a cell to gene delivery by the method of the present invention can be determined by assays for a reporter gene. A marker gene such as that encoding β-galactosidase (β-gal), chloramphenicol acetyl transferase (CAT), etc. is used for convenience to determine whether a protein can be expressed in a particular recombinant construct delivered by the present method. In addition, the quantity and duration of expression can be assayed. The use of, for example, neomycin resistance to determine the efficacy of gene delivery has been described in human testing with the desired gene. Thus, the skilled artisan, based on this disclosure can readily determine the efficacy of delivery of a particular vector construct in a particular target tissue and host using the method of the present invention.

The genetic material (nucleic acids) that is delivered to the target cell using the method of the present invention can be genes, for example, those that encode a variety of proteins including anticancer and antiviral agents. Such genes include those encoding various hormones, growth factors, enzymes, cytokines, receptors, MHC molecules and the like. The term "genes" includes nucleic acid sequences both exogenous and endogenous to cells into which the vector containing the gene of interest can be introduced.

Of particular interest for use in gene delivery are those genes encoding polypeptides either absent, produced in diminished quantities or produced in a mutant form in individuals suffering from a genetic disease. Such genetic diseases include retinoblastoma, Wilms tumor, adenosine deaminase deficiency (ADA), thalassemias, cystic fibrosis, Sickle cell disease, Huntington's disease, Duchenne's muscular dystrophy, Phenylketonuria, Lesch-Nyhan syndrome, Gaucher's disease, Tay-Sach's disease, and the like.

Additionally, it is of interest to use genes encoding tumor suppressor genes (e.g., retinoblastoma gene), TNF, TGF-β, TGF-α, hemoglobin, interleukins, GM-CSF, G-CSF, M-CSF, human growth hormone, co-stimulatory factor B7, insulin, factor VIII, factor IX, PDGF, EGF, NGF, EPO, β-globin and the like, as well as biologically active muteins of these proteins. Genes for delivery to target cells can be from a variety of species; however, preferred species sources for genes of interest are those species into which the gene of interest is to be inserted using the method of the present invention.

The gene can further encode a product that regulates expression of another gene product or blocks one or more steps in a biological pathway, such as the sepsis pathway. In addition, the gene can encode a toxin fused to a polypeptide, e.g., a receptor ligand or an antibody that directs the toxin to a target such as a tumor cell or a virus. Similarly, the gene can encode a protein that provides a therapeutic effect to a diseased tissue or organ.

Basic techniques for operably inserting genes into expression vectors are known to those skilled in the art. See, Sambrook et al., MOLECULAR CLONING: A LABORATORY MANUAL, 2 nd ed., Cold Spring Harbor Laboratory, Cold Spring Harbor, N.Y. (1989); Ausubel et al. (eds.), CURRENT PROTOCOLS IN MOLECULAR BIOLOGY, John Wiley and Sons (1987), both incorporated herein by reference.

Several possible vector systems are available for the expression of the gene in the mammalian cell that has been transformed according to the method of the present invention expression. These vector systems are well known to those skilled in the art. For example, one class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes can be selected by also introducing one or more markers which allow selection of host cells which contain the expression vector. The marker can provide for prototrophy to an auxotrophic host, biocide resistance, e.g., antibiotics, or resistance to heavy metals, such as copper or the like. The selectable marker gene can either be directly linked to the DNA sequences to be expressed, or introduced into the same cell by co-transformation. Additional elements can also be needed for optimal synthesis of mRNA. These elements can include splice signals, as well as transcription promoters, enhancers, and termination signals. The cDNA expression vectors incorporating such elements include those described by Okayama, H., *Mol. Cell. Biol.* 3:280 (1983), and others.

Single Chain Polypeptides

The invention relates to the discovery that single-chain antigen-binding proteins ("SCA") or single-chain variable fragments of antibodies ("sFv") having basic amino acid tails, have significant utility beyond that of the non basic amino acid tailed single-chain antigen-binding proteins. In addition to maintaining an antigen binding site, this SCA protein has a basic amino acid region, such as oligo-lysine or oligo arginine or a combination thereof, according to the present invention as disclosed, supra, at the C-terminus or N-terminus which is capable of non-specific nucleic acid binding thus enabling the basic amino acid tailed SCA polypeptide to act as a carrier to deliver nucleic acid to cells. Accordingly, the invention is directed to monovalent and multivalent SCA proteins having an oligo-lysine tail, compositions of monovalent and multivalent basic amino acid tailed SCA proteins, methods of making and purifying monovalent and multivalent basic amino acid tailed SCA proteins, and uses for the basic amino acid tailed SCA proteins. The invention is also directed to SCA proteins containing basic amino acid regions having a diagnostic or therapeutic agent bound to the basic amino acid linked polypeptide.

The terms "single-chain antigen-binding molecule" (SCA) or "single-chain Fv" (sFv) are used interchangeably. They are structurally defined as comprising the binding portion of a first polypeptide from the variable region of an antibody $V_L$ (or $V_H$), associated with the binding portion of a second polypeptide from the variable region of an antibody $V_H$ (or $V_L$), the two polypeptides being joined by a peptide linker linking the first and second polypeptides into a single polypeptide chain, such that the first polypeptide is N-terminal to the linker and second polypeptide is C-terminal to the first polypeptide and linker. The single polypeptide chain thus comprises a pair of variable regions connected by a polypeptide linker. The regions can associate to form a functional antigen-binding site, as in the case wherein the regions comprise a light-chain and a heavy-chain variable region pair with appropriately paired complementarity determining regions (CDRs). In this case, the single-chain protein is referred to as a "single-chain antigen-binding protein" or "single-chain antigen-binding molecule."

Single-chain Fvs can and have been constructed in several ways. Either $V_L$ is the N-terminal domain followed by the linker and $V_H$ (a $V_L$-Linker-$V_H$ construction) or $V_H$ is the N-terminal domain followed by the linker and $V_L$ ($V_H$-Linker-$V_L$ construction). The preferred embodiment contains $V_L$ in the N-terminal domain (see, Anand, N.N., et al., *J Biol. Chem.* 266:21874–21879 (1991)). Alternatively, multiple linkers have also been used. Several types of sFv proteins have been successfully constructed and purified, and have shown binding affinities and specificities similar to the antibodies from which they were derived.

A description of the theory and production of single-chain antigen-binding proteins is found in Ladner et al., U.S. Pat. Nos. 4,946,778, 5,260,203, 5,455,030 and 5,518,889, and in Huston et al., U.S. Pat. No. 5,091,513 ("biosynthetic antibody binding sites" (BABS)), all incorporated herein by reference. The single-chain antigen-binding proteins produced under the process recited in the above patents have binding specificity and affinity substantially similar to that of the corresponding Fab fragment.

Typically, the Fv domains have been selected from the group of monoclonal antibodies known by their abbreviations in the literature as 26-10, MOPC 315, 741F8, 520C9, McPC 603, D1.3, murine phOx, human phOx, RFL3.8 sTCR, 1A6, Se155-4,18-2-3,4-4-20, 7A4-1, B6.2, CC49, 3C2,2 c, MA-15C5/$K_{12}G_0$, Ox, etc. (see, Huston, J. S. et al., *Proc. Natl. Acad. Sci. USA* 85:5879–5883 (1988); Huston, J. S. et al., *SIM News* 38(4) (Supp.):11 (1988); McCartney, J. et al., *ICSU Short Reports* 10:114 (1990); McCartney, J. E. et al., unpublished results (1990); Nedelman, M. A. et al., *J Nuclear Med.* 32 (Supp.):1005 (1991); Huston, J. S. et al., In: *Molecular Design and Modeling. Concepts and Applications, Part B*, edited by J. J. Langone, Methods in Enzymology 203:46–88 (1991); Huston, J. S. et al., In: *Advances in the Applications of Monoclonal Antibodies in Clinical Oncology*, Epenetos, A. A. (Ed.), London, Chapman & Hall (1993); Bird, R. E. et al., *Science* 242:423–426 (1988); Bedzyk, W. D. et al., *J Biol. Chem.* 265:18615–18620 (1990); Colcher, D. et al., *J Nat. Cancer Inst.* 82:1191–1197 (1990); Gibbs, R. A. et al., *Proc. Natl. A cad. Sci. USA* 88:4001–4004 (1991); Milenic, D. E. et al., *Cancer Research* 51:6363–6371 (1991); Pantoliano, M. W. et al., *Biochemistry* 30:10117–10125 (1991); Chaudhary, V. K. et al., *Nature* 339:394–397 (1989); Chaudhary, V. K. et al., *Proc. Natl. Acad. Sci. USA* 87:1066–1070 (1990); Batra, J. K. et al., *Biochem. Biophys. Res. Comm.* 171:1–6 (1990); Batra, J. K. et al., *J Biol. Chem.* 265:15198–15202 (1990); Chaudhary, V. K. et al., *Proc. Natl. Acad. Sci. USA* 87:9491–9494 (1990); Batra, J. K. et al., *Mol. Cell. Biol.* 11:2200–2205 (1991); Brinkmann, U. et al., *Proc. Natl. Acad. Sci. USA* 88:8616–8620 (1991); Seetharam, S. et al., *J Biol. Chem.* 266:17376–17381 (1991); Brinkmann, U. et al., *Proc. Natl. Acad. Sci. USA* 89:3075–3079 (1992); Glockshuber, R. et al., *Biochemistry* 29:1362–1367 (1990); Skerra, A. et al., *Bio/Technol.* 9:273–278 (1991); Pack, P. et al., *Biochemistry* 31:1579–1534 (1992); Clackson, T. et al., *Nature* 352:624–628 (1991); Marks, J. D. et al.,*J. Mol. Biol.* 222:581–597 (1991); Iverson, B. L. et al., *Science* 249:659–662 (1990); Roberts, V. A. et al., *Proc. Natl. Acad. Sci. USA* 87:6654–6658 (1990); Condra, J. H. et al., *J Biol. Chem.* 265:2292–2295 (1990); Laroche, Y. et al., *J Biol. Chem.* 266:16343–16349 (1991); Holvoet, P. et al., *J. Biol. Chem.* 266:19717–19724 (1991); Anand, N. N. et al,*J. Biol. Chem.* 266:21874–21879 (1991); Fuchs, P. et al., *Bio/Technol.* 9:1369–1372 (1991); Breitling, F. et al., *Gene* 104:104–153 (1991); Seehaus, T. et al., *Gene* 114:235–237 (1992); Takkinen, K. et al., *Protein Engng.* 4:837–841 (1991); Dreher, M. L. et al., *J. Immunol. Methods* 139:197–205 (1991); Mottez, E. et al., *Eur. J. Immunol.* 21:467–471 (1991); Traunecker, A. et al., *Proc. Natl. Acad. Sci. USA* 88:8646–8650 (1991); Traunecker, A. et al.,*EMBO J.* 10:3655–3659 (1991); Hoo, W. F. S. et al, *Proc. Natl. Acad. Sci. USA* 89:4759–4763 (1993)).

Linkers of the invention used to construct sFv polypeptides are designed to span the C-terminus of $V_L$ (or neighboring site thereof) and the N-terminus of $V_H$ (or neighboring site thereof). The preferred length of the peptide linker should be from 2 to about 50 amino acids. In each particular case, the preferred length will depend upon the nature of the polypeptides to be linked and the desired activity of the linked fusion polypeptide resulting from the linkage. Generally, the linker should be long enough to allow the resulting linked fusion polypeptide to properly fold into a conformation providing the desired biological activity.

Where conformational information is available, as is the case with sFv polypeptides discussed below, the appropriate linker length can be estimated by consideration of the 3-dimensional conformation of the substituent polypeptides and the desired conformation of the resulting linked fusion polypeptide. Where such information is not available, the appropriate linker length can be empirically determined by testing a series of linked fusion polypeptides with linkers of varying lengths for the desired biological activity. Such linkers are described in detail in WO 94/12520, incorporated herein by reference.

Preferred linkers used to construct sFv polypeptides have between 10 and 30 amino acid residues. The linkers are designed to be flexible, and it is recommended that an underlying sequence of alternating Gly and Ser residues be used. To enhance the solubility of the linker and its associated single chain Fv protein, three charged residues can be included, two positively charged lysine residues (K) and one negatively charged glutamic acid residue (E). Preferably, one of the lysine residues is placed close to the N-terminus of $V_H$, to replace the positive charge lost when forming the peptide bond of the linker and the $V_H$. Such linkers are described in detail in U.S. patent application Ser. No. 08/224,591, filed Apr. 7, 1994, incorporated herein by reference. See also, Whitlow, M., et al., *Protein Engng.* 7:1017–1026 (1994). It should also be noted that a basic amino acid region having lysine and arginine residues could also be used in the linker for the sFv polypeptides of the present invention.

For multivalent sFvs, the association of two or more sFvs is required for their formation. Although, multivalent sFvs can be produced from sFvs with linkers as long as 25 residues, they tend to be unstable. Holliger, P., et al., *Proc. Natl. Acad. Sci. USA* 90:6444–6448 (1993), have recently demonstrated that linkers 0 to 15 residues in length facilitate the formation of divalent Fvs. See, Whitlow, M., et al., *Protein Engng.* 7:1017–1026 (1994); Hoogenboom, H. R., *Nature Biotech.* 15:125–126(1997). Such multivalent sFvs are described in detail in WO 93/11161, herein incorporated by reference.

Furthermore, single-chain and multivalent immunoeffector antigen-binding fusion proteins have also been designed and constructed. Such single-chain and multivalent immunoeffector antigen-binding fusion proteins provide the binding capability of the antigen binding protein combined with the immunoeffector or cytolytic function fusion partner, such as TNF, PLAP, IL-2, GM-CSF and the like. Such single-chain and multivalent immunoeffector antigen-binding fusion proteins are described in detail in U.S. Pat. No. 5,763,733, incorporated by reference.

The object of the present invention is to produce an sFv having a nucleic acid binding region comprising basic amino acid residues. The nucleic acid binding region can comprise a sequence that is rich in basic amino acids such as lysine, arginine and combinations thereof. This region will contain enough basic amino acids to obtain the requisite overall positive charge on the sFv for nucleic acid binding. These nucleic acid binding regions can be at the C-terminal region, N-terminal region or both of the sFv. The nucleic acid binding regions can be generated by mutating one or a plurality of amino acid residue(s) or by adding a block of basic amino acid residues to the C-terminal region, N-terminal region or both of the sFv. The sFv can have a region rich in basic amino acids, an oligo-Lys, oligo-Arg or combination thereof as a tail such that the basic amino acid rich region, oligo-Lys or oligo-Arg residues are sufficient to bind nucleic acids and the polypeptide binds an antigen (i.e., the polypeptide's ability to bind an antigen is not disrupted).

Preferably, the nucleic acid binding region of the single-chain antigen-binding polypeptide comprises at least 2 to 8 groups of eight consecutive Lys residues, Arg residues or a combination thereof, wherein each group of eight consecutive lysine, arg or lys/arg residues is separated from adjacent groups by 0–20 amino acid residues. More preferably, the nucleic acid binding region of the single-chain antigen-binding polypeptide comprises at least 2 to 6 groups of eight consecutive Lys residues, Arg residues or a combination thereof, wherein each group of eight consecutive lysine, arg or lys/arg residues is separated from adjacent groups by 0–20 amino acid residues. Still more preferably, the nucleic acid binding region of the single-chain antigen-binding polypeptide comprises at least 2 to 4 groups of eight consecutive Lys residues, Arg residues or a combination thereof, wherein each group of eight consecutive lysine, arg or lys/arg residues is separated from adjacent groups by 0–20 amino acid residues. More preferably, the nucleic acid binding region of the single-chain antigen-binding polypeptide comprises at least 2 to 3 groups of eight consecutive Lys residues, Arg residues or a combination thereof, wherein each group of eight consecutive lysine, arg or lys/arg residues is separated from adjacent groups by 0–20 amino acid residues. Still more preferably, the nucleic acid binding region of the single-chain antigen-binding polypeptide has at least 2 groups of eight consecutive Lys residues, Arg residues or a combination thereof, wherein each group of eight consecutive lysine, arg or lys/arg residues is separated from adjacent groups by 0–20 amino acid residues.

Alternatively, the nucleic acid binding regions of the single-chain antigen-binding polypeptide of the present invention can be represented by the following formulas: 1) (KKKKKKKK)m (X)n (KKKKKKKK) (SEQ ID NO: 8), wherein K is lysine, m is an integer between 1 and 7 and n is an integer between 0 and 20; 2) (RRRRRRRR)m (X)n (RRRRRRRR) (SEQ ID NO: 9), wherein R is Arginine, m is an integer between 1 and 7 and n is an integer between 0 and 20; 3) (RKRKRKRK)m (X)n (RKRKRKRK) (SEQ ID NO: 10), wherein K is lysine R is arginine such that the K and R residues either alternate or are in random order, m is an integer between 1 and 7 and n is an integer between 0 and 20; and 4) (RRRRRRRR)m (X)n (KKKKKKKK) (SEQ ID NO: 11), wherein K is lysine, R is arginine, m is an integer between 1 and 7 and n is an integer between 0 and 20. Preferably, the DNA binding regions of the single-chain antigen-binding polypeptide of the present invention can be represented by the following formulas: 1) (KKKKKKKK)m (X)n (KKKKKKKK) (SEQ ID NO: 8), wherein K is lysine, m is an integer between 1 and 5 and n is an integer between 0 and 20; 2) (RRRRRRRR)m (X)n (RRRRRRRR) (SEQ ID NO: 9), wherein R is Arginine, m is an integer between 1 and 5 and n is an integer between 0 and 20; 3) (RKRKRKRK)m (X)n (RKRKRKRK) (SEQ ID NO: 10), wherein K is lysine R is arginine such that the K and R residues either alternate or are in random order, m is an integer between 1 and 5 and n is an integer between 0 and 20; and 4) (RRRRRRRR)m (X)n (KKKKKKKK) (SEQ ID NO: 11), wherein K is lysine, R is arginine, m is an integer between 1 and 5 and n is an integer between 0 and 20.

More preferably, the nucleic acid binding regions of the single-chain antigen-binding polypeptide of the present invention can be represented by the following formulas: 1) (KKKKKKKK)m (X)n (KKKKKKKK) (SEQ ID NO: 8), wherein K is lysine, m is an integer between 1 and 3 and n is an integer between 0 and 20; 2) (RRRRRRRR)m (X)n (RRRRRRRR) (SEQ ID NO: 9), wherein R is Arginine, m is an integer between 1 and 3 and n is an integer between 0 and 20; 3) (RKRKRKRK)m (X)n (RKRKRKRK) (SEQ ID NO: 10), wherein K is lysine R is arginine such that the K and R residues either alternate or are in random order, m is an integer between 1 and 3 and n is an integer between 0 and 20; and 4) (RRRRRRRR)m (X)n (KKKKKKKK) (SEQ ID NO: 11), wherein K is lysine, R is arginine, m is an integer between 1 and 3 and n is an integer between 0 and 20.

Still more preferably, the nucleic acid binding regions of the single-chain antigen-binding polypeptide of the present invention can be represented by the following formulas: 1) (KKKKKKKK)m (X)n (KKKKKKKK) (SEQ ID NO: 8), wherein K is lysine, m is an integer between 1 and 2 and n is an integer between 0 and 20; 2) (RRRRRRRR)m (X)n (RRRRRRRR) (SEQ ID NO: 9), wherein R is Arginine, m is an integer between 1 and 2 and n is an integer between 0 and 20; 3) (RKRKRKRK)m (X)n (RKRKRKRK) (SEQ ID NO: 10), wherein K is lysine R is arginine such that the K and R residues either alternate or are in random order, m is an integer between 1 and 2 and n is an integer between 0 and 20; and 4) (RRRRRRRR)m (X)n (KKKKKKKK) (SEQ ID NO: 11), wherein K is lysine, R is arginine, m is an integer between 1 and 2 and n is an integer between 0 and 20.

More preferably, the nucleic acid binding regions of the single-chain antigen-binding polypeptide of the present invention can be represented by the following formulas: 1) (KKKKKKKK)m (X)n (KKKKKKKK) (SEQ ID NO: 8), wherein K is lysine, m is 1 and n is an integer between 0 and 20; 2) (RRRRRRRR)m (X)n (RRRRRRRR) (SEQ ID NO: 9), wherein R is Arginine, m is 1 and n is an integer between 0 and 20; 3) (RKRKRKRK)m (X)n (RKRKRKRK) (SEQ ID NO: 10), wherein K is lysine R is arginine such that the K and R residues either alternate or are in random order, m is 1 and n is an integer between 0 and 20; and 4) (RRRRRRRR)m (X)n (KKKKKKKK) (SEQ ID NO: 11), wherein K is lysine, R is arginine, m is 1 and n is an integer between 0 and 20. Even more preferably, the single-chain antigen-binding polypeptide has the region rich in basic amino acid residues, oligo lysine residues, oligo arginine residues or combination thereof, configured such that the number of groups of consecutive Lys and or Arg residues is no higher than that which would result in an unstable polynucleotide encoding the single-chain antigen-binding polypeptide or significantly reduce the efficiency of translation of the polynucleotide encoding the single-chain antigen-binding polypeptide.

These novel sFv proteins can be conjugated to activated polyethylene glycol (PEG) such that the PEG modification occurs preferentially at specifically engineered sites. See, U.S. application Ser. No. 09/069,842, filed on Apr. 30,1998.

A further object of the invention is to produce monovalent and multivalent sFvs having the oligo lysine tails of the present invention. For multivalent sFv, the association of two or more sFvs is required for their formation. For example, multivalent sFvs can be generated by chemically crosslinking two sFvs with C-terminal cysteine residues (Cumber et al., *J Immunol.* 149:120–126 (1992)) and by linking two sFvs with a third polypeptide linker to form a dimeric Fv (George et al., *J. Cell. Biochem.* 15E:127 (1991)). Details for producing multivalent sFvs by aggregation are described in Whitlow, M., et al., *Protein Engng.* 7:1017–1026 (1994). Multivalent antigen-binding fusion proteins of the invention can be made by any process, but preferably according to the process for making multivalent antigen-binding proteins set forth in WO 93/11161, incorporated herein by reference.

Synthesis of the Minimal Nucleic Acid Binding Regions

In the present invention, a region rich in basic amino acid residues, oligo-Lys, oligo-Arg or oligo-Lys/Arg nucleic acid binding region can occur in the C-terminus or N-terminus of the sFv polypeptide. Preferably, the nucleic acid binding region will occur in the C-terminus of the sFv polypeptide. The site at the C-terminus was chosen to be as far from the antigen binding residues of the polypeptide as possible so as to prevent disruption of the antigen-binding site.

Site-directed mutagenesis is used to change the native protein sequence of the single-chain antigen-binding protein to one that incorporates the regions rich in Lys, Arg, oligo-Lys, oligo-Arg or oligo-Lys/Arg residues. The mutant protein gene is placed in an expression system, such as bacterial cells, yeast or other fungal cells, insect cells or mammalian cells. The mutant protein can be purified by standard purification methods.

Oligonucleotide-directed mutagenesis methods for generating the minimal basic amino acid nucleic acid binding regions or the present invention and related techniques for mutagenesis of cloned DNA are well known in the art. See, Sambrook et al, MOLECULAR CLONING: A LABORATORY MANUAL, 2nd ed., Cold Spring Harbor Laboratory, Cold Spring Harbor, N.Y. (1989); Ausubel et al. (eds.), CURRENT PROTOCOLS IN MOLECULAR BIOLOGY, John Wiley and Sons (1987), both incorporated herein by reference. A preferred oligonucleotide-directed mutagenesis method for the present invention is according to Ho et al., *Gene* 77:51–59 (1989), incorporated herein by reference.

Hosts and Vectors for the Preparation of the sFv Polypeptides

After mutating the nucleotide sequence of the sFv, the mutated DNA can be inserted into a cloning vector for further analysis, such as for confirmation of the DNA sequence. To express the polypeptide encoded by the mutated DNA sequence, the DNA sequence is operably linked to regulatory sequences controlling transcriptional expression and introduced into either a prokaryotic or eukaryotic host cell.

Although sFvs are typically produced by prokaryotic host cells, eukaryotic cells can also be used as host cells. Preferred host cells include *E. coli*, yeast or other fungal cells, insect cells or mammalian cells. Standard protein purification methods can be used to purify these mutant proteins. Only minor modification to the native protein's purification scheme can be required.

Also provided by the invention are DNA molecules such as purified genetic sequences or plasmids or vectors encoding the sFv of the invention that have engineered region(s) containing high content of basic amino acids, oligo-Lys, oligo-Arg or oligo-Lys/Arg residues capable of non-specific nucleic acid binding. The DNA sequence for the sFv polypeptide can be chosen so as to optimize production in organisms such as prokaryotes, yeast or other fungal cells, insect cells or mammalian cells.

The DNA molecule encoding an sFv having a region rich in basic amino acid residues, oligo-Lys, oligo-Arg, or oligo-Lys/Arg residues which comprise the minimal DNA binding region can be operably linked into an expression vector and introduced into a host cell to enable the expression of the engineered sFv protein by that cell. A DNA sequence encoding an sFv having a region rich in basic amino acid residues, oligo-Lys, oligo-Arg, or oligo-Lys/Arg regions can be recombined with vector DNA in accordance with conventional techniques. Recombinant hosts as well as methods of using them to produce single chain proteins of the invention are also provided herein.

The expression of such sFv proteins of the invention can be accomplished in procaryotic cells. Preferred prokaryotic hosts include, but are not limited to, bacteria such as Bacilli, Streptomyces and *E. coli.*

Eukaryotic hosts for cloning and expression of such sFv proteins of the invention include plant cells, insect cells, yeast, fungi, and mammalian cells (such as, for example, human or primate cells) either in vivo, or in tissue culture. A preferred host for the invention is Pichia pastoris. As discussed in more detail below, the inventors have demonstrated excellent yields of the sFv proteins having the regions rich in basic amino acid residues according to the present invention using Pichia pastoris.

The appropriate DNA molecules, hosts, methods of production, isolation and purification of monovalent, multivalent and fusion forms of proteins, especially sFv polypeptides, are thoroughly described in the prior art, such as, e.g., U.S. Pat. No. 4,946,778, which is fully incorporated herein by reference.

The sFv encoding sequence having the minimal DNA binding region comprising oligo-Lys, oligo-Arg, or oligo-Lys/Arg residues and an operably linked promoter can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication, the expression of the desired sFv protein can occur through the transient expression of the introduced sequence. Alternatively, permanent expression can occur through the integration of the introduced sFv sequence into the host chromosome.

In one embodiment, the sFv sequence can be integrated into the host cell chromosome. Cells which have stably integrated the introduced DNA into their chromosomes can be selected by also introducing one or more markers which allow for selection of host cells which contain the sFv sequence and marker. The marker can complement an auxotrophy in the host (such as his4, leu2, or ura3, which are common yeast auxotrophic markers), or can confer biocide resistance, e.g., antibiotics, or resistance to heavy metals, such as copper, or the like. The selectable marker gene can either be directly linked to the sFv DNA sequence to be expressed, or introduced into the same cell by co-transfection.

In another embodiment, the introduced sequence will be incorporated into a plasmid vector capable of autonomous replication in the recipient host cell. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

Any of a series of yeast vector systems can be utilized. Examples of such expression vectors include the yeast 2-micron circle, the expression plasmids YEP13, YCP and YRP, etc., or their derivatives. Such plasmids are well known in the art (Botstein et al., Miami Wntr. Symp. 19:265–274 (1982); Broach, J. R., In: The Molecular Biology of the Yeast Saccharomyces: Life Cycle and Inheritance, Cold Spring Harbor Laboratory, Cold Spring Harbor, N.Y., p. 445–470 (1981); Broach, J. R., Cell 28:203–204 (1982)).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes can be selected by also introducing one or more markers which allow selection of host cells which contain the expression vector. The marker can provide prototrophy to an auxotrophic host, biocide resistance, e.g., antibiotics, or resistance to heavy metals, such as copper or the like. The selectable marker gene can either be directly linked to the DNA sequences to be expressed, or introduced into the same cell by co-transformation. Additional elements can also be needed for optimal synthesis of mRNA. These elements can include splice signals, as well as transcription promoters, enhancers, and termination signals. The cDNA expression vectors incorporating such elements include those described by Okayama, H., Mol. Cell. Biol. 3:280 (1983), and others.

Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Preferred vectors for expression in Pichia are pHIL-S1 (Invitrogen Corp.) and pIC9 (Invitrogen Corp.). Other suitable vectors will be readily apparent to the skilled artisan.

Once the vector or DNA sequence containing the sFv constructs of the present invention has been prepared for expression, the DNA constructs can be introduced or transformed into an appropriate host. Various techniques can be employed, such as transformation, transfection, protoplast fusion, calcium phosphate precipitation, electroporation, or other conventional techniques. After the cells have been transformed with the recombinant DNA (or RNA) molecule, the cells are grown in media and screened for appropriate activities. Expression of the sequence results in the production of the mutant sFv for use in the gene delivery method of the present invention.

Expression and Purification of sFv Proteins

The inventors have demonstrated excellent yields of the oligo-lysine tailed sFv of the present invention, particularly CC49-16K, secreted from Pichia postoris. This provides a means of making enough of the DNA-binding sFv for commercial gene therapy applications. In addition, the inventors have discovered a novel purification procedure for the oligo-lysine tailed sFv which is ionically bound to the nucleic acids from lysed cells in the fermentation broth. The oligo-lysine tailed sFv is initially found in the cell pellet fraction, but can be readily released by salt treatment in excellent yield and purity.

The vectors pIC9 and pHIL-S1, and host strain GS115 were obtained from Invitrogen Corporation and all cloning and expression work was performed as described in the "Pichia Expression Kit Instruction, Manual" supplied by Invitrogen. Clone number designations for CC49/218 sFv variants are as follows.

| Clone # | Plasmid # | Vector | C-terminal lysine # |
|---|---|---|---|
| EN266(5) | pEN262(5) | pHIL-S1 | 8 K |
| EN266(7) | pEN262(7) | pHIL-S1 | 16 K |
| EN281(1) | pEN278(1) | pIC9 | 8 K |
| EN282 | pEN278(5) | pIC9 | 16 K |

Figure 5:
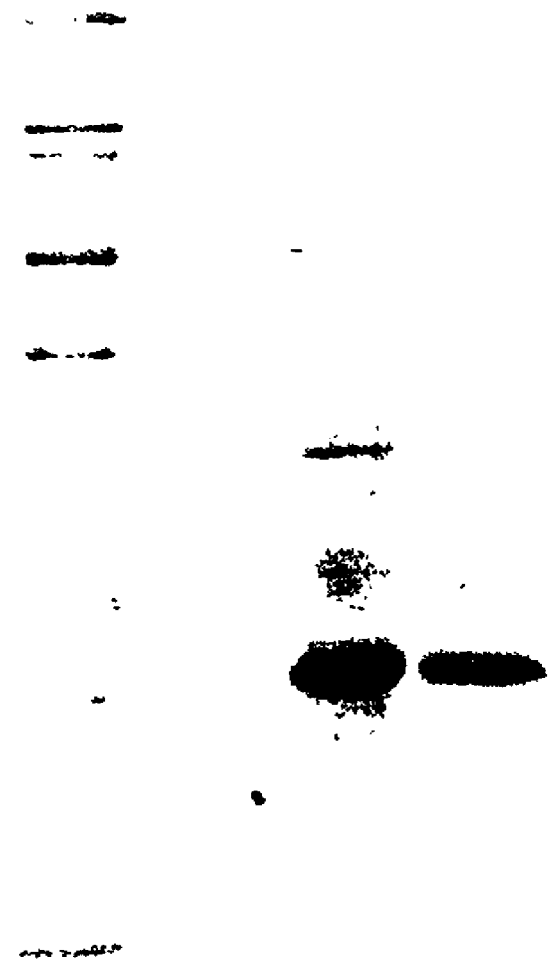

Expression levels were >20 mg/L of protein as estimated by SDS-PAGE and Western analysis. The 8K (8 lysine tail)

version and 16K (16 lysine tail) version of the sFv migrated on SDS-PAGE at positions approximately 1.6 KD and 3.3 KD greater in mass in agreement with the predicted size from their polypeptide sequences. The sFv proteins were all soluble in shake-flask experiments, but often were associated with the cell pellet in fermentation cultures. The sFv was dissociated from the pellet by high salt wash (1.5 M NaCl, 20 mM Tris-HCl, pH 8.0 at room temperature for 2 hours). Consequently, this provided a very good purification step. Fermentation cultures contain substantial amounts of lysed cells and the 16K sFv variant proteins appear to bind to nucleic acids present in the fermentation medium. Significantly, the native sFv does not become cell associated. The Coomassie Blue stained SDS-PAGE gel of FIG. 5, is an example of the excellent expression of CC4916K 266(7) and the ability of salt treatment to solubilize and purify the sFv of the present invention.

Western analysis confirmed the major sFv molecules at about 26.5 Kd for native sFv and about 30 Kd for CC49-16K sFv. This experiment was performed as follows: (1) 100 ml of expression medium of EN266(7) from shake-flask culture was frozen and thawed, then centrifuged at 3,000 rpm, room temperature (RT) for 30 min.; (2) EN266 cell pellet was resuspended in 2 ml of 1.5 M NaCl, 20 mM Tris-HCl, pH 8.0, RT, 2 hrs.; (3) the sample was centrifuged as in (1) and the supernatant was dialyzed against 0.15 M NaCl, 10 mM Tris-HCl, pH 8.0 at 4° C. overnight; (4) the protein content of the supernantant was quantitated at A280 to be about 1.5 mg/ml; and (5) 30 µl of the supernatant were loaded on SDS-PAGE gels for Coomassie Blue staining and Western analysis.

The Western analysis was performed as follows: Immunoblotting procedures for transfer of proteins from gels to nitrocellulose membranes by the semi-dry method were performed as described in Harlow, E., & Lane, D., *Antibodies*: A Laboratory Manual, Cold Spring Harbor Laboratory Press, Cold Spring Harbor, N.Y., (1988). Blot development was also performed according to the procedures in this manual. Briefly, the blotted membranes were blocked in 1% BSA blocking reagent in PBS at room temperature for 2 hr; washed 3× with PBS; and incubated with 3% BSA in PBS with a 1:1,000 dilution of rabbit anti-CC49/218 SCA antibody at 4° C. overnight. Next, a 3% BSA in PBS solution containing a 1:1000 dilution of horseradish peroxidase conjugated goat anti-rabbit IgG was used in a 1 hr incubation at room temperature. After washing with PBS, the membranes were developed with TMBM-500 (MOSS, Inc.) at room temperature for 1 min.

The purified sFvs of the present invention can be stored as a stabilized protein composition having increased frozen storage stability as described in detail in U.S. Pat. No. 5,656,730, incorporated herein by reference.

Administration

Administration of basic amino acid tailed sFv-nucleic acid conjugates of the invention for ex vivo and in vivo delivery of nucleic acids to mammalian cells will be by analogous methods to sFv where the diagnostic or therapeutic principle is directly linked to the sFv or a loaded carrier is linked by random binding to amine or carboxyl groups on amino acid residues of the sFv in a non-site-specific manner.

Conjugates of the present invention (immunoconjugates) can be formulated according to known methods to prepare pharmaceutically useful compositions, such as by admixture with a pharmaceutically acceptable carrier vehicle. Suitable vehicles and their formulation are described, for example, in *Remington's Pharmaceutical Sciences*, 18th ed., Osol, A., ed., Mack, Easton Pa. (1990). In order to form a pharmaceutically acceptable composition suitable for effective administration, such compositions will contain a therapeutically effective amount of the immunoconjugate, either alone, or with a suitable amount of carrier vehicle.

The immunoconjugate can be provided to a patient by means well known in the art. Such means of introduction include subcutaneous means, intramuscular means, intravenous means, intra-arterial means, or parenteral means. Intravenous, intraarterial or intrapleural administration is normally used for lung, breast, and leukemic tumors. Intraperitoneal administration is advised for ovarian tumors. Intrathecal administration is advised for brain tumors and leukemia. Subcutaneous administration is advised for Hodgkin's disease, lymphoma and breast carcinoma. Catheter perfusion is useful for metastatic lung, breast or germ cell carcinomas of the liver. Intralesional administration is useful for lung and breast lesions.

For therapeutic or diagnostic applications, compositions according to the invention can be administered parenterally in combination with conventional injectable liquid carriers such as sterile pyrogen-free water, sterile peroxide-free ethyl oleate, dehydrated alcohol, or propylene glycol. Conventional pharmaceutical adjuvants for injection solution such as stabilizing agent, solubilizing agents and buffers, such as ethanol, complex forming agents such as ethylene diamine tetraacetic acid, tartrate and citrate buffers, and high-molecular weight polymers such as polyethylene oxide for viscosity regulation can be added. Such compositions can be injected intramuscularly, intraperitoneally, or intravenously.

Further non-limiting examples of carriers and diluents include albumin and/or other plasma protein components such as low density lipoproteins, high density lipoproteins and the lipids with which these serum proteins are associated. These lipids include phosphatidyl choline, phosphatidyl serine, phosphatidyl ethanolamine and neutral lipids such as triglycerides. Lipid carriers also include, without limitation, tocopherol.

A typical regimen for preventing, suppressing, or treating various pathologies comprises administration of an effective amount of an sFv conjugate, administered over a period of one or several days, up to and including between one week and about 24 months.

It is understood that the dosage of the present invention administered in vivo or in vitro will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. See, e.g., Berkow et al., eds., *Merck Manual*, 16th edition, Merck and Co., Rahway, N.J. (1992); Goodman et al., eds., *Goodman and Gilman's The Pharmacological Basis of Therapeutics*, 8th edition, Pergamon Press, Inc., Elmsford, N.Y. (1990); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston (1985), Katzung, *Basic and Clinical Phamacology*, Appleton and Lange, Norwalk, Conn. (1992), which references and references cited therein, are entirely incorporated herein by reference.

The total dose required for each treatment can be administered by multiple doses or in a single dose. Effective amounts of a diagnostic/pharmaceutical compound or composition of the present invention are from about 0.001 μg to about 100 mg/kg body weight, administered at intervals of 4–72 hours, for a period of 2 hours to 5 years, or any range or value therein, such as 0.01–1.0, 1.0–10,10–50 and 50–100 mg/kg, at intervals of 1–4,6–12,12–24 and 24–72 hours, for a period of 0.5, 1.0–2.0, 2.0–4.0 and 4.0–7.0 days, or 1, 1–2, 2–4, 4–52 or more weeks, or 1, 2, 3–10, 10–20, 20–60 or more years, or any range or value therein.

Preparations for parenteral administration include sterile aqueous or non-aqueous solutions, suspensions, and emulsions, which can contain auxiliary agents or excipients which are known in the art. See, e.g., Berker, supra, Goodman, supra, Avery, supra and Ebadi, supra, which are entirely incorporated herein by reference, including all references cited therein.

Pharmaceutical compositions comprising at least one type of sFv conjugate having a basic amino acid rich region according to the invention, or, 1, 2, 3, 4, 5, 6, 7, 8, 9 or 10 types of sFv conjugates, of the present invention can be contained in an amount effective to achieve its intended purpose. In addition to at least one sFv conjugate, a pharmaceutical composition can contain suitable pharmaceutically acceptable carriers, such as excipients, carriers and/or auxiliaries which facilitate processing of the active compounds into preparations which can be used pharmaceutically.

Pharmaceutical compositions can also include suitable solutions for administration intravenously, subcutaneously, dermally, orally, mucosally or rectally, and contain from about 0.01 to 99 percent, preferably from about 20 to 75 percent of active component (i.e., the DNA binding sFv conjugate) together with the excipient. Pharmaceutical compositions for oral administration include tablets and capsules. Additional lipid and lipoprotein drug delivery systems that can be included herein are described more fully in *Annals N.Y. Acad. Sci.* 507:775–88, 98–103, and 252–271, which disclosure is hereby incorporated by reference.

For example, the sFvs of the present invention can be prepared as a pharmaceutically acceptable, single-chain antigen-binding protein composition having increased frozen-storage stability, as described in detail in U.S. Pat. No 5,656,730, incorporated by reference.

Having now generally described this invention, the same will be better understood by reference to certain specific examples, which are included for the purpose of illustration and not intended to be limiting unless otherwise specified

EXAMPLES

Example 1

Demonstration of DNA Binding

In order to demonstrate the DNA binding capabilities of the C-terminal oligo-lysine tailed SCAs the following experiment was performed. The CC49/218 SCA and A33/218 SCA having a 16 lysine ("16K") C-terminal tail and the CC49/218 SCA and A33/218 SCA having a 8 lysine ("8K") C-terminal tail were expressed from Pichia.

Genetic construction of the sFv proteins having an oligo-lysine C-terminal tails was performed by first introducing a unique BstEII restriction site (GGTNACC) into VH codons including positions 108, 109 and 110 (Kabat numbers) by standard site directed mutagenesis. This mutation does not alter the encoded amino acids and is accomplished by simply changing the position 108 codon from TCA (Ser) to TCG (Ser), a single base change. The unique BstEII restriction site can be digested with the restriction enzyme BstEII and a synthetic linker having BstEII compatible overhangs is ligated into the site. The synthetic linker used consists of two complementary oligonucleotides

```
5' GTC ACC GTC TCC AAA AAG AAG AAA AAA AAG AAA AAG 3'   (SEQ ID NO: 12); and

5' GT GAC CTT TTT CTT TTT TTT CTT CTT TTT GAA GAC G 3'  (SEQ ID NO: 13).
```

This linker can be inserted as a single copy or as two or more tandem copies due to the compatible overhangs. In the case of the 16 lysine tail sFv, two tandem copes of this linker are presented as confirmation by DNA sequencing of the genetic construction.

The proteins were assayed for DNA binding function in a standard Gel Shift assay (Mistry et al. *Biotechniques* 22:718–729 (1997)). The A33/218 SCA having a 16 lysine C-terminal tail (EN266 (3F)) was incubated with plasmid pFLAG-1(International Biotechnologies, Inc.) (0.5 μg) in DNA binding buffer (0.01M Tris, pH8.0, 0.15M NaCl). The samples were then electrophoresed on the gel shown in FIG. 4. The results show that this SCA protein had DNA binding capability. The CC49/218 SCA having a 16 lysine C-terminal tail (EN278(5)) also bound DNA. The results in FIG. 4 show that supercoiled DNA species (faster moving species) was more effectively complexed by the SCA molecules than the nicked linear DNA species and are consistent with the results shown by Mistry et al. The CC49/218 SCA and A33/218 SCA having a 8 lysine C-terminal tail, however, did not show DNA binding capacity by this assay.

Example 2

Transfection of Mammalian Cells

In order to demonstrate the transfection of mammalian cells using the oligo-lysine single-chain antigen binding polypeptide of the present invention the following experiment can be performed.

CC49/218 sFv protein engineered to contain a 16 lysine tail (FIGS. 2A and B) is expressed and secreted by *Pichia pastoris* strain EN266. The protein is purified by standard cation and anion exchange chromatography well known to those skilled in the art. The protein is then concentrated by diafiltration. The sFv is incubated with reporter plasmid DNA, such as one of the pRL vectors (Promega Corp.). The sFv and plasmid DNA are incubated for 10–60 minutes in buffer (0.01M Tris, pH 8.0, 0.15M NaCl) in the following concentration ratio: 0.5 μg of pRL vector and 10 μg of sFv polypeptide. Controls for the transfection experiment are 1) CC49/218 sFv lacking the 16 lysine tail incubated with pRL vector and 2) plasmid alone.

The sFv/plasmid complex is then incubated with cultured LS-174T cells which are resuspended in the buffer (0.01 M Tris, pH 8.0, 0.15 M NaCl), for 10–60 minutes. The cells are then centrifuged at 2,000 rpm for five minutes and washed once with incubation buffer. The cells are next suspended in electroporation buffer (1xHBS: 20 mM HEPES, pH 7.05, 137 mM NaCl, 5 mM KCl, 0.7 mM $Na_2HPO_4$, 6 mM dextrose). One set of cells are subjected to electroporation using BTX Electro Cell Manipulator 600 System according to the manufacturer's instructions. Another cell of cells are examined for the spontaneous uptake of the sFv/plasmid complex by omitting the electroporation step. The success of transfection of the cells by the reporter plasmid is quantitated by luciferase assays performed according to the protocol described by Promega Corp., in Promega Notes #57.

Example 3

Demonstration of DNA Binding

Additional Gel Shift assays demonstrating the DNA binding capacity of CC49-16K (EN266(7)) and A33-16K were performed as follows. Experimental conditions are as in Example 1 except as follows.

CC49-16K (EN266(7)) was purified by DEAE column chromatography and fraction 8 (OD280=3.6) was dialyzed versus 0.15 M NaCl, 10 mM Tris-HCl, pH 8.0 at 4° C. overnight. Aliquots of the samples (0–90 µl) were mixed with 1 µl of plasmid Bluescript SK⁻ (3 ug/µl) and distilled water was added to a final volume of 100 µl. The samples were incubated at RT for 1 hr. Twenty µl of each sample were loaded and run on a 1.2% agarose gel, 100V, 2 hrs.

The A33-16K sample was incubated as in Example 1 except the plasmid used was pFLAG from IBI, Inc. (1 µg/µl) and incubation was done at RT for 1 hr.

Example 4

ELISA Assay

Figure 6:
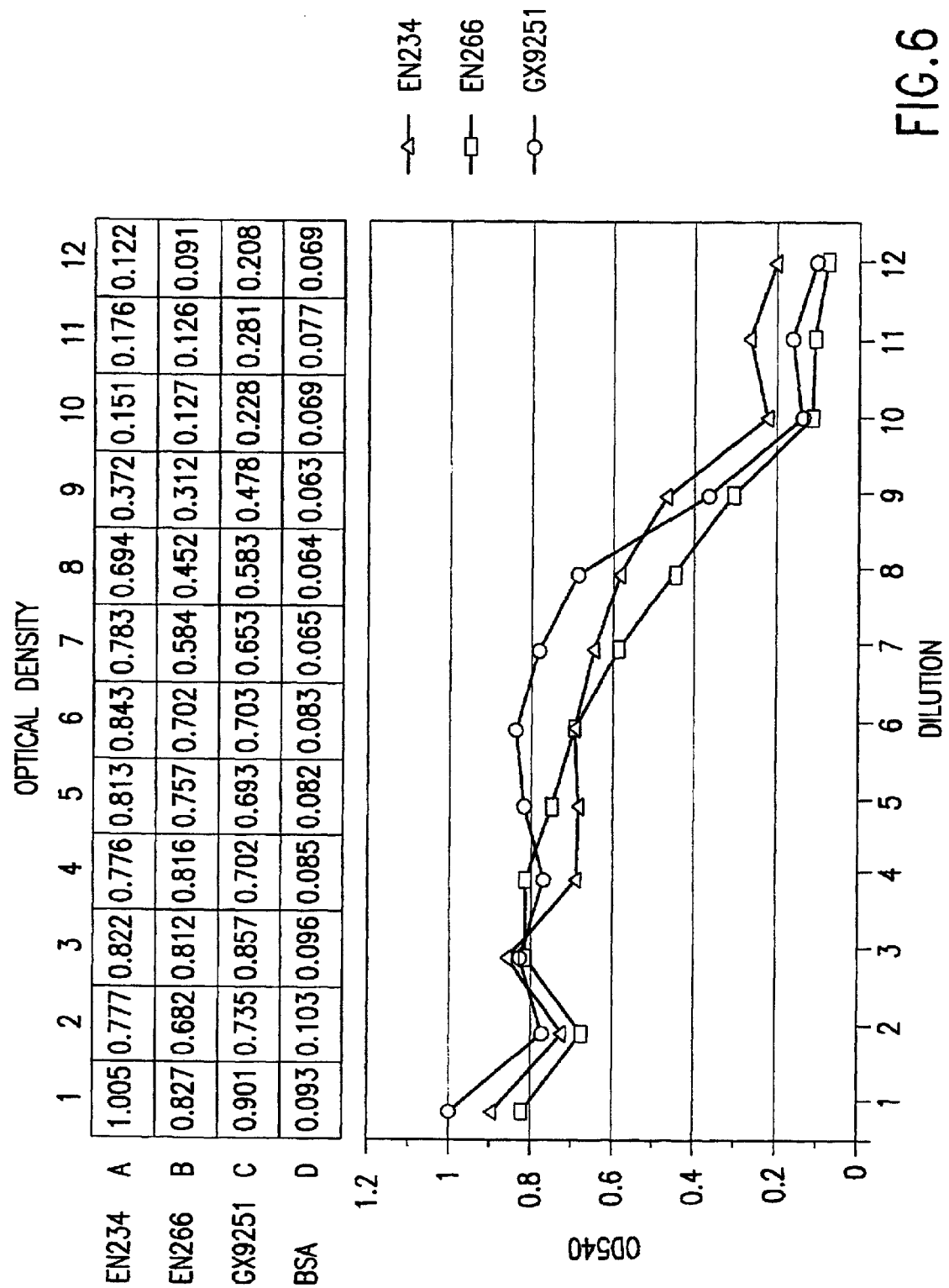
FIG. 6 shows an ELISA assay demonstrating retention of mucin-binding activity of the CC49-16K sFv EN266(7).

An ELISA assay demonstrating retention of mucin-binding activity of the CC49-16K sFv EN266(7) shown in FIG. 6 was performed as follows. The ELISA was performed by 1:2 serial dilutions of the sFv samples. Immunoassay procedures were performed using modifications of protocols from Harlow, E., & Lane, D., *Antibodies*: A Laboratory Manual, Cold Spring Harbor Laboratory Press, Cold Spring Harbor, N.Y., (1988). Direct binding assays were performed and a dose response curve was constructed. Bovine submaxillary mucin (250 ng per 100 µl well) antigen was used to coat microtiter plate wells (MaxiSorp, Nunc, VWR Scientific, Boston, Mass.). The EN266(7) or purified CC49/218 SCA proteins were diluted serially in PBS containing 1% BSA and incubated in the coated wells at 22° C. for 1 hr. After the plate was washed three times with PBS containing 0.05% Tween 20 (PBS-T), the bound SCA was detected by a 1 hr incubation with a secondary antibody (rabbit anti-CC49/218, 1:2000 dilution, 37° C.), followed by three PBS-T washes, and a 1 hr incubation at 37° C. with horseradish peroxidase conjugated goat anti-rabbit IgG antibody (1:2000 dilution). Plates were washed 3 times with PBS-T and were read at 540 nm following addition of 100 µl of 3',3',5',5'-tetramethylbenzidine (TMB).

EN234 is native CC49/218 sFv produced from Pichia. GX9251 is native CC49/218 sFv produced from *E. coli*. The BSA control is not plotted on the graph. These results indicate that antigen-binding activity of the sFv is not substantially altered in the sFv-16K variant protein.

In the next experiments, these oligo-lysine tailed sFv proteins were shown to be capable of gene delivery in vitro. First, these results demonstrate that CC49-16K sFv which is complexed with plasmid DNA adheres to TAG-72 antigen bearing LS174-T cells. Second, these results demonstrate that the CC49-16K sFv/plasmid complex can markedly enhance the LipofectAmine transfection of DNA into the LS174-T cells.

Example 5

Targeted DNA Delivery

Binding of CC49-16K sFv/plasmid DNA complex to LS174-T cells was demonstrated by in situ immunochemistry.

Experimental Protocol: LS174-T cells were grown in T75 tissue culture flasks in MEM medium containing 1× non-essential amino acids, 1× Earles' salts and 1% fetal bovine serum at 37° C. with 5% $CO_2$. Cells ($2\times10^6$ cells) in a T75 flask were treated with 1× trypsin/EDTA and split into four T75 flasks and incubated 16 hrs. The experimental procedure is as follows. (1)$8\times10^6$ LS174-T cells were collected by trypsin/EDTA digestion from the 4 T75 flasks. (2) The cells were centrifuged at 3,000 rpm at 4° C. (3) The supernatant was discarded and the cells were resuspended in PBS at 4° C. (4) The cells were centrifuged at 3,000 rpm, the supernatant discarded, and 2 ml of 1% paraformaldehyde (PFA) in PBS was added to the pellet on ice for 30 min. (5) The cells were washed with PBS, twice at 4° C. (6) The CC49-16K sFv and GX9251 samples were analyzed and quantitated by SDS-PAGE. (7) 5 µl (0.1 µg) of DIG-labeled (digoxigenin-labeled) pBR328 plasmid DNA (Boehringer Mannheim Cat. No. 1585 738) was mixed with 200 µl of native GX9251 CC49/218 sFv (15 µg/ml) or with 200 µl of EN266(7) CC49-16K sFv (approx. 5 µg/ml) at RT for 30-min. (8) The LS174-T cells were added to the DIG-labeled pBR328 plasmid/sFv mixture and incubated at RT for 30 min. (9) The cells were washed twice with PBS. (10) The cells were centrifuged and resuspended in 200 µl of PBS containing 1% BSA and a 1:100 dilution of anti-digoxigenin-AP (alkaline phosphatase) Fab (Boehringer Mannheim Cat. No. 1093 274). Incubation was done at RT for 30 min. (11). The cells were washed twice with PBS. (12). The cells were centrifuged and the pellet was resuspended in 100 µl of Fast Red solution (one tablet of Fast Red was dissolved in 500 µl of 0.1M Tris-HCl, 0.15 M NaCl, pH 8.3; Fast Red Tablets are obtained from Boehringer Mannheim, Cat. No. 1 496 549). Incubation was at RT for 30 min. (13). 50 µl of each sample were pipetted onto a glass slide, covered with a cover slip, and observed immediately under a microscope (Nikon) using a 20× object lense and photographed.

GX9251 CC49/218 sFv sample was used in the complex with the pBR328 plasmid DNA. Background staining was minimal. EN266(7) CC49-16K sFv sample was used in the complex with the plasmid DNA. Positive red staining was visually intense. Staining was more apparent in regions of cell debris presumably due to the nature of the cell surface TAG-72 antigen which is repetitive and easily shed making it more densely concentrated in these regions. Since the detection signal results from the presence of the DIG-labeled pBR328 plasmid DNA, this experiment demonstrated (1) that the CC49-16K sFv can target plasmid to LS174-T cells but native CC49/218 sFv can not do so and (2) that the affinity of the plasmid for the CC49-16K sFv proteins is sufficient to remain complexed through several washing steps.

Example 6

Cell Transfection

This example demonstrates the transfection of LS174-T cells by reporter plasmid pSEAP2 using CC49-16K sFv as carrier.

Protocol: The SEAP Reporter plasmid system (PT3057-2) was obtained from Clontech (Palo Alto, Calif.) and used according to the supplier's instructions. The pSEAP2 plasmid expresses a gene encoding a secreted alkaline phosphatase which serves as a reporter for successful transfection of a cultured cell. The LIPOFECTAMINE PLUS reagent which enhances transfection of DNA was obtained from Life Technologies (Gaithersburg, Md. Cat. No. 10964-013) and used according to the supplier's instructions. As initial controls, DNA binding of the CC49-16K to pSEAP2 was demonstrated by Gel Shift experiments as described in Examples 1 and 3 and a suitable sFv to plasmid ratio was determined as stated below. Plasmid pSEAP2 was also shown to be successfully transfected into LS174-T cells by the Lipofectamine method using the recommended protocol. Furthermore, the AP reporter chemiluminescence signal could be quantitated by exposure to an X-ray film such that the strength of the signals (grains on the film) were proportional to the amount of plasmid added over a 0–5 µg range.

The demonstration of CC49-16K sFv targeted transfection of LS 174-T by plasmid pSEAP2 employed the following protocol. All test articles were done in duplicate. (1) LS174-T cells ($3 \times 10^6$) were plated on each well of a six well (Costar) plate in DMGM medium with 10% fetal bovine serum (FBS), at 37° C. with 5% $CO_2$ overnight. (2) The cells were washed with HBSS. (3) In separate microfuge tubes, (a) 5 µl (5 µg) of plasmid pSEAP2 and 50 µl (about 50 µg) of EN266(7) CC49-16K sFv; OR (b) 5 µl (5 µg) of plasmid pSEAP2 and 50 µl (about 50 µg) of EN234 CC49/218 native sFv; OR (c) 5 µl (5 µg) of plasmid pSEAP and 50 µl of water were mixed and incubated at room temperature for 30 min in 200 µl of DMEM medium. (4) The sFv/plasmid mixtures were added onto the LS174-T cells and incubated at 37° C. for 60 min. (5) The cells were washed twice with HBSS. (6) 12 µl of PLUS reagent (Life Technologies Lipofectamine Plus kit) were mixed with 100 µl of DMEM medium and added onto the LS174-T cells, then incubated at 37° C. for 30 min. (7) 8 µl of Lipofectamine was mixed into 100 µl of DMEM and added to each well of the LS174-T plate, then incubated at 37° C. for 30 min. (8) 0.8 ml of DMEM was added to each well and incubated at 37° C. for 3 hrs. (9) 100 µl of FBS and 1 ml of DMGM with 10% FBS were added. Incubation continued at 37° C. with 5% $CO_2$ for 2 days. (10) 1 ml of culture medium was transferred from each well into 1.5 ml microfuge tubes. (11) The cells were centrifuged in a microfuge to pellet the cells and debris. (12) The supernatants from each tube were transferred into a Centricon 10 (Amicon Inc.) and concentrated to a volume of 0.1 ml. (13) 25 µl of each sample were mixed with 75 µl of 1× dilution buffer (Clontech) and incubated at 65° C. for 30 min. (14) The samples were cooled to room temperature and 100 µl of assay buffer (Clontech) were added with incubation at room temperature for 5 min. (15) 100 µl of 1.25 mM CSPD with 1× chemiluminescence enhancer (Clontech) were mixed into each tube. (16) 150 µl of each sample were transferred into individual wells of a DYNATECH microFLUOR plate. (17) The microtiter plate was overlayed with X-ray film and the film was exposed for 3 hrs at room temperature.

Figure 7A:
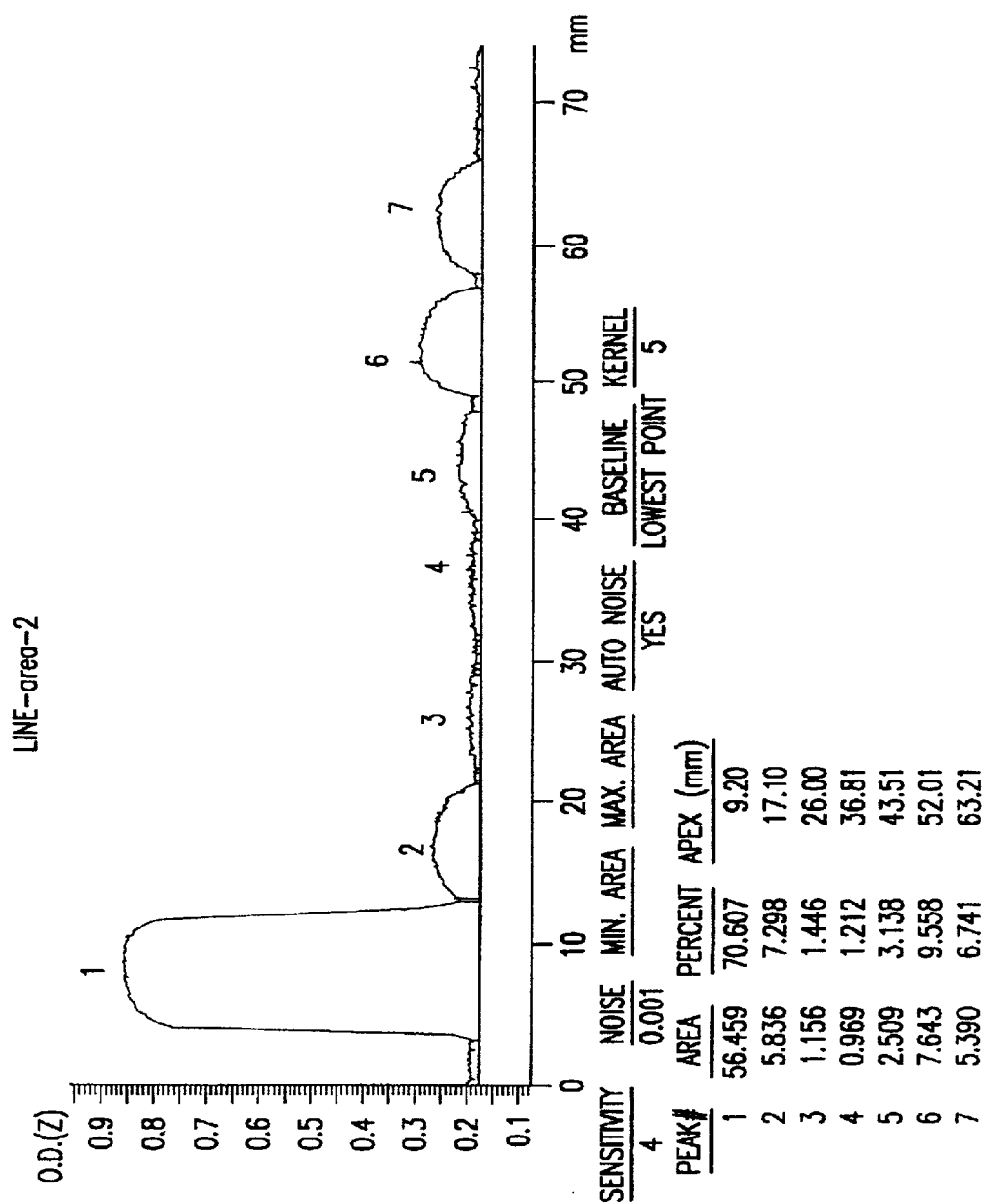
FIGS. 7A and 7B show the results of the transfection of LS174-T cells by reporter plasmid pSEAP using CC49-16K sFv as carrier.
Figure 7B:
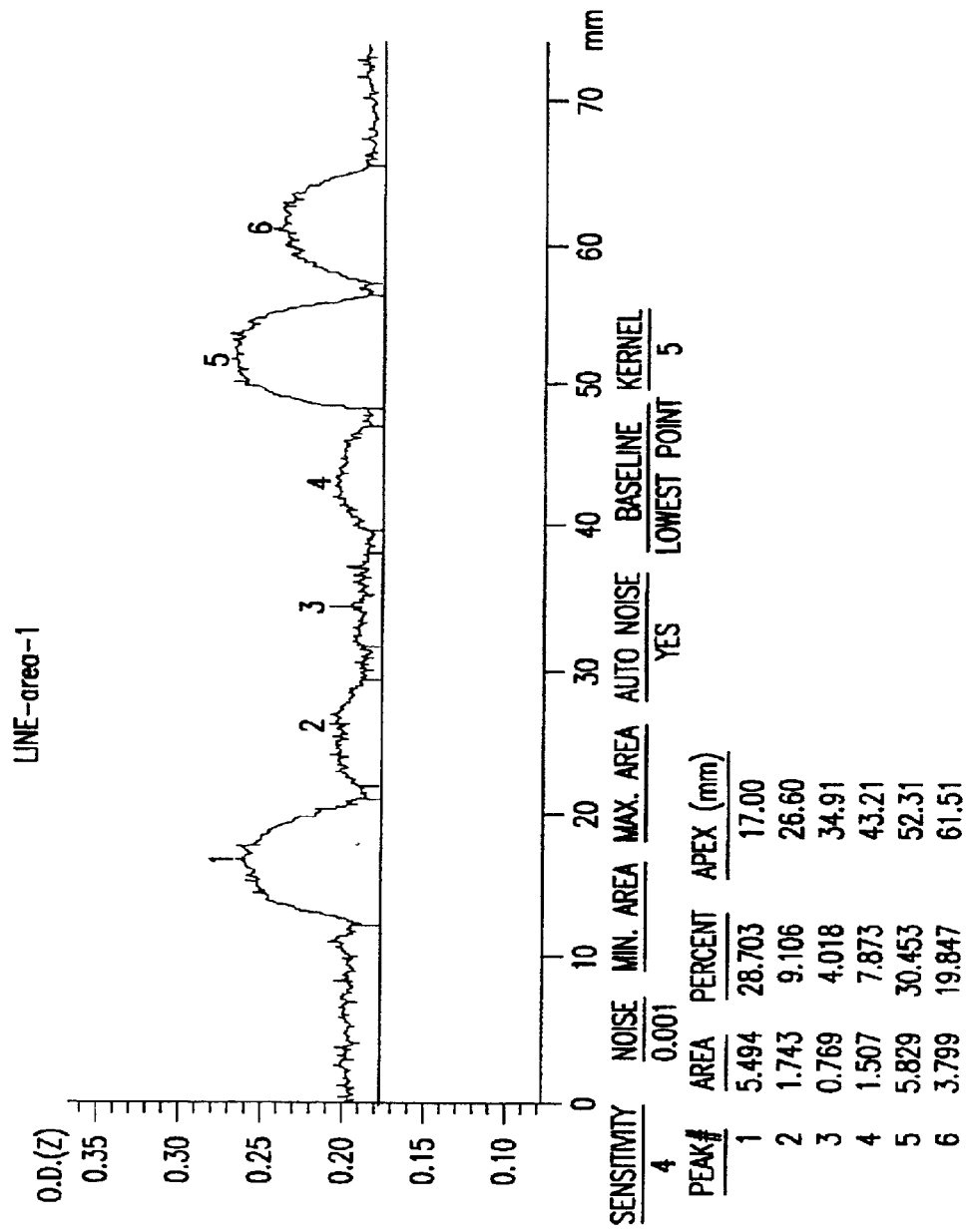

The results are shown in FIGS. 7A and 7B. Lanes in the exposed x-ray film with duplicate lanes top and bottom are as follows. Lanes: 1. Positive control with 0.5 µl of pure placental alkaline phosphatase in overexposed well; 2. Standard (Lipofectamine Plus) transfection of pSEAP2 without sFv (i.e., condition c above) where washing steps (5) above are omitted; 3. LS174-T cell control with no added plasmid or sFv; 4. pSEAP plasmid transfection without sFv (condition c above); 5. pSEAP2 plasmid plus EN234 native sFv as described for condition b above; 6. pSEAP2 plasmid plus EN266(7) CC49-16K sFv as described for condition a above; 7. Same as lane 6 except both protocol steps 5 (washings) and 7 (Lipofectamine) are omitted; 8. Control with DMEM medium alone. FIGS. 7A and 7B show the area quantitations of the x-ray film which were preformed by densitometry scanning using a Molecular Dynamics PD-SI laser scanner. Quantitation data are provided for both top (FIG. 7A; lane 8 was not scanned) and bottom (FIG. 7B; lanes 1 and 8 were not scanned) rows. Note that CC49-16K sFv (lane 6) promotes transfection about 8-fold over plasmid-alone control levels (lane 4) in this experiment.

Summary of transfection experiments: The area quantitation results demonstrate that plasmid pSEAP can not efficiently transfect the cells in the absence of CC49-16K sFv (lane 4). The plasmid is simply washed off the cells in step 5. However, CC49-16K inclusion (lane 6) allows the sFv/plasmid complexes to remain attached to the cells and transfection proceeds as efficiently as in a standard transfection protocol (lane 2) where the washing steps are omitted. Lane 5 shows that native sFv has a minor but detectable enhancement of transfection. This may be due to nonspecific association of this very basic (pI ~9.3) sFv with the negatively charged DNA. Lane 7 suggests that the CC49-16K/plasmid complex with no Lipofectamine added is slightly better than standard (+lipofectamine) transfection (with no washing at step 5).

Example 7

Synthesis of DNA Binding Regions in Other sFvs

Oligonucleotide-directed mutagenesis, synthetic linker ligation or polymerase chain reaction can be employed to create oligo-lysine or oligo-arginine C-terminal tail in an sFv having a Kabat consensus $V_K I/218/V_H III$ sFv (FIG. 8), C6.5/218 sFv (FIG. 9), and A33/218 sFv. Amino acid assignments of the Kabat consensus $V_K I/218/V_H III$ sFv and A33/218 sFv are according to Kabat et al., *Sequences of Proteins of Immunological Interest*, pp. 108 & 331, 5th ed., U.S. Dept. Health and Human Services, Bethesda, Md. (1991), where the assigned amino acid residue at a position is the most commonly occurring amino acid at that position. Amino acid assignments of the wild-type C6.5 variable domains are according to Schier, R., et al., *J. Mol. Biol.* 255:28–43 (1996).

The mutated sFvs are individually ligated into the Pichia transfer plasmid pHIL-S1 or pIC9 (Invitrogen Corp.) and transformed into *Pichia pastoris*. Detailed protocols for these procedures are presented in the Pichia Expression Kit Instruction Manual Cat. No. X1710-01 (1994) from Invitrogen Corporation. The sFv variants are placed behind a yeast signal sequence in these constructions and the integrated sFv in the yeast transformants are tested for secretion of the sFv proteins. Evaluation of expression is done by Coomassie staining of SDS-PAGE gels.

Although the foregoing refers to particular preferred embodiments, it will be understood that the present invention is not so limited. It will occur to those skilled in the art that various modifications can be made to the disclosed

What is claimed is:

1. A method of delivering a nucleic acid to a cell located in vitro comprising:
   (a) providing a single-chain antigen-binding polypeptide capable of delivering nucleic acids to a cell comprising:
      (i) a first polypeptide comprising the antigen binding portion of the variable region of an antibody heavy or light chain;
      (ii) a second polypeptide comprising the antigen binding portion of the variable region of an antibody heavy or light chain; wherein each polypeptide has a C-terminus and an N-terminus, and
      (iii) a peptide linker linking the first and second polypeptides into a single chain polypeptide,
      wherein the single-chain antigen-binding polypeptide comprises an antigen binding site and a nucleic acid binding region, and the nucleic acid binding region comprises sufficient residues selected from the group consisting of oligo Lys, oligo Arg, and an oligopeptide that is a combination thereof, to bind a nucleic acid to the single-chain antigen-binding polypeptide;
   (b) allowing a nucleic acid to bind to the single-chain antigen-binding polypeptide and
   (c) transforming a cell located in vitro with the nucleic acid bound single-chain antigen-binding polypeptide.

2. The method of claim 1 wherein the nucleic acid binding region is located adjacent to a terminus selected from the group consisting of the C-terminus of the first polypeptide, the C-terminus of the second polypeptide, the N-terminus of the first polypeptide, the N-terminus of the second polypeptide, and combinations thereof.

3. The method of claim 1 wherein the nucleic acid binding region comprises at least 2 to 8 groups of eight consecutive residues selected from the group consisting of Lys residues, Arg residues and a combinations thereof, wherein each group of eight consecutive Lys, Mg or combinations thereof is separated from adjacent groups by 0–20 amino acid residues.

4. The method of claim 1 wherein the nucleic acid binding region comprises at least 2 to 6 groups of eight consecutive residues selected from the group consisting of Lys residues, Mg residues and a combinations thereof, wherein each group of eight consecutive Lys, Mg or combinations thereof is separated from adjacent groups by 0–20 amino acid residues.

5. The method of claim 1 wherein the nucleic acid binding region comprises at least 2 to 4 groups of eight consecutive residues selected from the group consisting of Lys residues, Arg residues and a combinations thereof, wherein each group of eight consecutive Lys, Arg or combinations thereof is separated from adjacent groups by 0–20 amino acid residues.

6. The method of claim 1 wherein the nucleic acid binding region comprises at least 2 to 3 groups of eight consecutive residues selected from the group consisting of Lys residues, Mg residues and a combinations thereof, wherein each group of eight consecutive Lys, Mg or combinations thereof is separated from adjacent groups by 0–20 amino acid residues.

7. The method of claim 1 wherein the nucleic acid is a vector for expressing a protein in the transformed cell.

8. The method of claim 1 wherein the transformed cell is a mammalian cell.

9. The method of claim 1 wherein the cell is obtained from a human or animal, and wherein the cell is reimplanted into said human or animal after transformation with the nucleic acid.

10. The method of claim 1 wherein the nucleic acid vector is a plasmid.

11. The method of claim 1 wherein the nucleic acid vector comprises a reporter gene.

12. The method of claim 1 wherein the cell is obtained from an animal selected from the group consisting of horses, cows, pigs, dogs, cats and primates.

13. The method of claim 1 wherein the single-chain antigen-binding polypeptide binds to an antigen of the cell.

14. The method of claim 1 wherein the single-chain antigen-binding polypeptide is a CC 49 sFv protein.

15. The method of claim 1 wherein step (c) is conducted in the presence of a transfection agent.

16. The method claim 15 wherein the transfection agent is LIPOFECTAMINE PLUS™.

* * * * *

UNITED STATES PATENT AND TRADEMARK OFFICE
CERTIFICATE OF CORRECTION

PATENT NO. : 6,764,853 B2
DATED : July 20, 2004
INVENTOR(S) : Filpula, David R. et al.

It is certified that error appears in the above-identified patent and that said Letters Patent is hereby corrected as shown below:

Column 47,
Line 65, "Mg" should read -- Arg --;

Column 48,
Lines 33, 47 and 48, "Mg" should read -- Arg --; and
Line 67, "polypeptide binds" should read -- polypeptide specifically binds --.

Signed and Sealed this

Eighth Day of February, 2005

JON W. DUDAS
*Director of the United States Patent and Trademark Office*